(12) United States Patent
Somasundaram et al.

(10) Patent No.: US 11,208,468 B2
(45) Date of Patent: Dec. 28, 2021

(54) METHODS AND COMPOSITIONS FOR TREATING MELANOMA

(71) Applicant: The Wistar Institute of Anatomy and Biology, Philadelphia, PA (US)

(72) Inventors: Rajasekharan Somasundaram, West Chester, PA (US); Meenhard Herlyn, Wynnewood, PA (US); Dorothee Herlyn, Wynnewood, PA (US)

(73) Assignee: The Wistar Institute of Anatomy and Biology, Philadelphia, PA (US)

( * ) Notice: Subject to any disclaimer, the term of this patent is extended or adjusted under 35 U.S.C. 154(b) by 0 days.

(21) Appl. No.: 15/998,913

(22) PCT Filed: Feb. 16, 2017

(86) PCT No.: PCT/US2017/018051
§ 371 (c)(1),
(2) Date: Aug. 16, 2018

(87) PCT Pub. No.: WO2017/142988
PCT Pub. Date: Aug. 24, 2017

(65) Prior Publication Data
US 2019/0276517 A1 Sep. 12, 2019

Related U.S. Application Data

(60) Provisional application No. 62/296,705, filed on Feb. 18, 2016.

(51) Int. Cl.
| | | |
|---|---|---|
| *A61K 38/00* | (2006.01) | |
| *C07K 7/00* | (2006.01) | |
| *C07K 14/82* | (2006.01) | |
| *A61P 35/00* | (2006.01) | |
| *A61K 9/127* | (2006.01) | |
| *A61K 35/15* | (2015.01) | |
| *A61K 38/17* | (2006.01) | |
| *A61K 39/395* | (2006.01) | |
| *C07K 16/28* | (2006.01) | |
| *C12N 9/12* | (2006.01) | |
| *A61K 39/00* | (2006.01) | |

(52) U.S. Cl.
CPC ........... *C07K 14/82* (2013.01); *A61K 9/127* (2013.01); *A61K 35/15* (2013.01); *A61K 38/1709* (2013.01); *A61K 39/39541* (2013.01); *A61P 35/00* (2018.01); *C07K 16/2818* (2013.01); *C12N 9/12* (2013.01); *C12Y 207/11001* (2013.01); *A61K 2039/505* (2013.01); *C07K 2317/76* (2013.01); *C07K 2319/00* (2013.01)

(58) Field of Classification Search
None
See application file for complete search history.

(56) References Cited

U.S. PATENT DOCUMENTS

| | | | |
|---|---|---|---|
| 6,083,716 A | 7/2000 | Wilson et al. | |
| 7,247,472 B2 | 7/2007 | Wilson et al. | |
| 7,696,179 B2 | 4/2010 | Lieberman et al. | |
| 7,803,611 B2 | 9/2010 | Roelvink et al. | |
| 7,811,993 B2 | 10/2010 | Herlyn et al. | |
| 2010/0203109 A1* | 8/2010 | Herlyn .................. | A61P 35/00 424/450 |
| 2013/0289253 A1 | 10/2013 | Luescher et al. | |

FOREIGN PATENT DOCUMENTS

| | | |
|---|---|---|
| CN | 104780976 A | 7/2015 |
| CN | 104968675 A | 10/2015 |
| WO | WO1994/01139 | 1/1994 |
| WO | WO1996/02269 | 2/1996 |
| WO | WO2005/071093 | 8/2005 |
| WO | WO2007/002811 | 1/2007 |
| WO | WO2012/044999 | 4/2012 |
| WO | WO 2015/028461 A2 | 2/2014 |
| WO | WO 2014/043441 A1 | 3/2014 |

OTHER PUBLICATIONS

Melanoma, Merck Manuals melanoma accessed Jan. 13, 2021 at URL merckmanuals.com/professional/dermatologic-disorders/cancers-of-the-skin, pp. 1-12. (Year: 2021).*
Whipple, "BRAFv600e melanoma cells secrete factors that activate stromal fibroblasts and enhance tumorigenecity," British Journal of cancer 111:1162-1633 (2014) (Year: 2014).*
Chen et al., "BRAFV600E Negatively Regulates the AKT Pathway in Melanoma Cell Lines," Plos ONE 7: e42598, pp. 1-9 (2012) (Year: 2012).*
Somasundaram, R. et al. "Human Leukocyte Antigen-A2-Restricted CTL Responses to Mutated BRAF Peptides in Melanoma Patients," Cancer research, vol. 66, No. 6, Mar. 15, 2006, p. 3287-3293, XP55624201, US ISSN: 0008-5472, doi: 10.1158/0008-5472.CAN-05-1932.

(Continued)

*Primary Examiner* — Julie Ha
*Assistant Examiner* — Kristina M Hellman
(74) *Attorney, Agent, or Firm* — Colleen Schaller; Howson & Howson LLP

(57) ABSTRACT

Compositions and methods for treating melanoma are provided. Compositions include $BRAF_{V600E}$-based peptides, alone or admixed with T helper peptides. Other compositions include nucleic acid sequences encoding the $BRAF_{V600E}$-based peptides, alone or admixed with nucleic acid sequences T helper peptides. Dendritic cells pretreated with the $BRAF_{V600E}$-based peptides, alone or admixed with T helper peptides, are also provided. These compositions are useful to treat melanoma, optionally co-administered with antibodies to checkpoint inhibitors or molecules that mimic the action of such antibodies.

14 Claims, 4 Drawing Sheets
Specification includes a Sequence Listing.

(56) References Cited

OTHER PUBLICATIONS

European Search Report, dated Jan. 20, 2020, in corresponding European Patent Application No. 17753785.9, filed Aug. 31, 2018.
Lauer et al, Constitutive Activation of the PrfA Regulon Enhances the Potency of Vaccines Based on Live-Attenuated and Killed but Metabolically Active Listeria monocytogenes Strainsl, Infect. Immunity, 76(8):3742-53 (Aug. 2008).
Manjunath, N. et al, Lentiviral delivery of short hairpin RNAs. Adv Drug Deliv Rev., 61(9): 732-745 (Jul. 2009).
Porter et al., Chimeric Antigen Receptor-Modified T Cells in Chronic Lymphoid Leukemia. N Engl J Med. Aug. 25, 2011;365(8):725-33.
Radice, E. et al, Enhancement of the Immunostimulatory Functions of Ex Vivo-Generated Dendritic Cells from Early-Stage Colon Cancer Patients by Consecutive Exposure to Low Doses of Sequential-Kinetic-Activated IL-4 and IL-12. A Preliminary Study. Aug. 2015, Translational Oncol., 8(4):327-338.
International Search Report, dated Jun. 29, 2017, in corresponding International Patent Application No. PCT/US17/18051, filed Feb. 16, 2017.
Written Opinion, dated Jun. 29, 2017, in corresponding International Patent Application No. PCT/US17/18051, filed Feb. 16, 2017.
Office Action issued in corresponding Chinese Patent Application No. 201780024075.5, dated May 20, 2021.

* cited by examiner

SEQUENCE LISTING

<160> NUMBER OF SEQ ID NOS: 34

<210> SEQ ID NO 1
<211> LENGTH: 766
<212> TYPE: PRT
<213> ORGANISM: Homo sapiens

<400> SEQUENCE: 1

Met Ala Ala Leu Ser Gly Gly Gly Gly Gly Ala Glu Pro Gly Gln
1               5                   10                  15

Ala Leu Phe Asn Gly Asp Met Glu Pro Glu Ala Gly Ala Gly Ala Gly
            20                  25                  30

```
Ala Ala Ala Ser Ser Ala Ala Asp Pro Ala Ile Pro Glu Glu Val Trp
            35                  40                  45

Asn Ile Lys Gln Met Ile Lys Leu Thr Gln Glu His Ile Glu Ala Leu
 50                  55                  60

Leu Asp Lys Phe Gly Gly Glu His Asn Pro Pro Ser Ile Tyr Leu Glu
 65                  70                  75                  80

Ala Tyr Glu Glu Tyr Thr Ser Lys Leu Asp Ala Leu Gln Gln Arg Glu
                 85                  90                  95

Gln Gln Leu Leu Glu Ser Leu Gly Asn Gly Thr Asp Phe Ser Val Ser
            100                 105                 110

Ser Ser Ala Ser Met Asp Thr Val Thr Ser Ser Ser Ser Ser Ser Leu
            115                 120                 125

Ser Val Leu Pro Ser Ser Leu Ser Val Phe Gln Asn Pro Thr Asp Val
    130                 135                 140

Ala Arg Ser Asn Pro Lys Ser Pro Gln Lys Pro Ile Val Arg Val Phe
145                 150                 155                 160

Leu Pro Asn Lys Gln Arg Thr Val Val Pro Ala Arg Cys Gly Val Thr
                165                 170                 175

Val Arg Asp Ser Leu Lys Lys Ala Leu Met Met Arg Gly Leu Ile Pro
            180                 185                 190

Glu Cys Cys Ala Val Tyr Arg Ile Gln Asp Gly Glu Lys Lys Pro Ile
            195                 200                 205

Gly Trp Asp Thr Asp Ile Ser Trp Leu Thr Gly Glu Glu Leu His Val
    210                 215                 220

Glu Val Leu Glu Asn Val Pro Leu Thr Thr His Asn Phe Val Arg Lys
225                 230                 235                 240

Thr Phe Phe Thr Leu Ala Phe Cys Asp Phe Cys Arg Lys Leu Leu Phe
                245                 250                 255

Gln Gly Phe Arg Cys Gln Thr Cys Gly Tyr Lys Phe His Gln Arg Cys
            260                 265                 270

Ser Thr Glu Val Pro Leu Met Cys Val Asn Tyr Asp Gln Leu Asp Leu
    275                 280                 285

Leu Phe Val Ser Lys Phe Phe Glu His His Pro Ile Pro Gln Glu Glu
    290                 295                 300

Ala Ser Leu Ala Glu Thr Ala Leu Thr Ser Gly Ser Ser Pro Ser Ala
305                 310                 315                 320

Pro Ala Ser Asp Ser Ile Gly Pro Gln Ile Leu Thr Ser Pro Ser Pro
                325                 330                 335

Ser Lys Ser Ile Pro Ile Pro Gln Pro Phe Arg Pro Ala Asp Glu Asp
            340                 345                 350

His Arg Asn Gln Phe Gly Gln Arg Asp Arg Ser Ser Ser Ala Pro Asn
            355                 360                 365

Val His Ile Asn Thr Ile Glu Pro Val Asn Ile Asp Asp Leu Ile Arg
    370                 375                 380

Asp Gln Gly Phe Arg Gly Asp Gly Gly Ser Thr Thr Gly Leu Ser Ala
385                 390                 395                 400

Thr Pro Pro Ala Ser Leu Pro Gly Ser Leu Thr Asn Val Lys Ala Leu
                405                 410                 415

Gln Lys Ser Pro Gly Pro Gln Arg Glu Arg Lys Ser Ser Ser Ser Ser
            420                 425                 430

Glu Asp Arg Asn Arg Met Lys Thr Leu Gly Arg Arg Asp Ser Ser Asp
            435                 440                 445
```

```
Asp Trp Glu Ile Pro Asp Gly Gln Ile Thr Val Gly Gln Arg Ile Gly
    450                 455                 460
Ser Gly Ser Phe Gly Thr Val Tyr Lys Gly Lys Trp His Gly Asp Val
465                 470                 475                 480
Ala Val Lys Met Leu Asn Val Thr Ala Pro Thr Pro Gln Gln Leu Gln
                485                 490                 495
Ala Phe Lys Asn Glu Val Gly Val Leu Arg Lys Thr Arg His Val Asn
            500                 505                 510
Ile Leu Leu Phe Met Gly Tyr Ser Thr Lys Pro Gln Leu Ala Ile Val
        515                 520                 525
Thr Gln Trp Cys Glu Gly Ser Ser Leu Tyr His His Leu His Ile Ile
    530                 535                 540
Glu Thr Lys Phe Glu Met Ile Lys Leu Ile Asp Ile Ala Arg Gln Thr
545                 550                 555                 560
Ala Gln Gly Met Asp Tyr Leu His Ala Lys Ser Ile Ile His Arg Asp
                565                 570                 575
Leu Lys Ser Asn Asn Ile Phe Leu His Glu Asp Leu Thr Val Lys Ile
            580                 585                 590
Gly Asp Phe Gly Leu Ala Thr Glu Lys Ser Arg Trp Ser Gly Ser His
        595                 600                 605
Gln Phe Glu Gln Leu Ser Gly Ser Ile Leu Trp Met Ala Pro Glu Val
    610                 615                 620
Ile Arg Met Gln Asp Lys Asn Pro Tyr Ser Phe Gln Ser Asp Val Tyr
625                 630                 635                 640
Ala Phe Gly Ile Val Leu Tyr Glu Leu Met Thr Gly Gln Leu Pro Tyr
                645                 650                 655
Ser Asn Ile Asn Asn Arg Asp Gln Ile Ile Phe Met Val Gly Arg Gly
            660                 665                 670
Tyr Leu Ser Pro Asp Leu Ser Lys Val Arg Ser Asn Cys Pro Lys Ala
        675                 680                 685
Met Lys Arg Leu Met Ala Glu Cys Leu Lys Lys Arg Asp Glu Arg
    690                 695                 700
Pro Leu Phe Pro Gln Ile Leu Ala Ser Ile Glu Leu Leu Ala Arg Ser
705                 710                 715                 720
Leu Pro Lys Ile His Arg Ser Ala Ser Glu Pro Ser Leu Asn Arg Ala
                725                 730                 735
Gly Phe Gln Thr Glu Asp Phe Ser Leu Tyr Ala Cys Ala Ser Pro Lys
            740                 745                 750
Thr Pro Ile Gln Ala Gly Gly Tyr Gly Ala Phe Pro Val His
        755                 760                 765

<210> SEQ ID NO 2
<211> LENGTH: 10
<212> TYPE: PRT
<213> ORGANISM: Artificial Sequence
<220> FEATURE:
<223> OTHER INFORMATION: synthetic peptide

<400> SEQUENCE: 2

Leu Ala Thr Glu Lys Ser Arg Trp Ser Gly
1               5                   10

<210> SEQ ID NO 3
<211> LENGTH: 14
<212> TYPE: PRT
<213> ORGANISM: Artificial Sequence
<220> FEATURE:
```

```
<223> OTHER INFORMATION: synthetic peptide
<220> FEATURE:
<221> NAME/KEY: MISC_FEATURE
<222> LOCATION: (1)..(2)
<223> OTHER INFORMATION: Xaa is absent, Ser, Gly or Cys for coupling to
      an additional peptide or protein
<220> FEATURE:
<221> NAME/KEY: MISC_FEATURE
<222> LOCATION: (4)..(4)
<223> OTHER INFORMATION: Xaa is a substituted or unsubstituted Ala, Leu,
      Met, Val, Pro or Gly
<220> FEATURE:
<221> NAME/KEY: MISC_FEATURE
<222> LOCATION: (5)..(5)
<223> OTHER INFORMATION: Xaa is a substituted or unsubstituted Thr or
      Ser
<220> FEATURE:
<221> NAME/KEY: MISC_FEATURE
<222> LOCATION: (7)..(7)
<223> OTHER INFORMATION: Xaa is a substituted or unsubstituted Lys, Arg
      or His
<220> FEATURE:
<221> NAME/KEY: MISC_FEATURE
<222> LOCATION: (8)..(8)
<223> OTHER INFORMATION: Xaa is a substituted or unsubstituted Ser or
      Thr
<220> FEATURE:
<221> NAME/KEY: MISC_FEATURE
<222> LOCATION: (9)..(9)
<223> OTHER INFORMATION: Xaa is a substituted or unsubstituted Arg, Lys,
      or His
<220> FEATURE:
<221> NAME/KEY: MISC_FEATURE
<222> LOCATION: (11)..(11)
<223> OTHER INFORMATION: Xaa is substituted or unsubstituted Thr, Val,
      Leu or Ser
<220> FEATURE:
<221> NAME/KEY: MISC_FEATURE
<222> LOCATION: (12)..(12)
<223> OTHER INFORMATION: Xaa is absent or is a substituted or
      unsubstituted Gly, Pro or Leu
<220> FEATURE:
<221> NAME/KEY: MISC_FEATURE
<222> LOCATION: (13)..(14)
<223> OTHER INFORMATION: Xaa is absent, or  Cys, Ser or Gly for coupling
      to an additional peptide or protein

<400> SEQUENCE: 3

Xaa Xaa Leu Xaa Xaa Glu Xaa Xaa Xaa Trp Xaa Xaa Xaa Xaa
1               5                   10

<210> SEQ ID NO 4
<211> LENGTH: 14
<212> TYPE: PRT
<213> ORGANISM: Artificial Sequence
<220> FEATURE:
<223> OTHER INFORMATION: synthetic peptide
<220> FEATURE:
<221> NAME/KEY: MISC_FEATURE
<222> LOCATION: (1)..(2)
<223> OTHER INFORMATION: Xaa is absent, Ser, Gly, Cys for coupling to an
      additional peptide or protein
<220> FEATURE:
<221> NAME/KEY: MISC_FEATURE
<222> LOCATION: (4)..(4)
<223> OTHER INFORMATION: Xaa is a substituted or unsubstituted Ile
<220> FEATURE:
<221> NAME/KEY: MISC_FEATURE
<222> LOCATION: (12)..(12)
<223> OTHER INFORMATION: Xaa is a hydrophobic amino acid
<220> FEATURE:
<221> NAME/KEY: MISC_FEATURE
<222> LOCATION: (13)..(14)
<223> OTHER INFORMATION: Xaa is absent, Ser, Gly, or Cys for coupling to
      an additional peptide or protein

<400> SEQUENCE: 4
```

```
Xaa Xaa Leu Xaa Thr Glu Lys Ser Arg Trp Ser Xaa Xaa Xaa
1               5                   10
```

<210> SEQ ID NO 5
<211> LENGTH: 14
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(2)
<223> OTHER INFORMATION: Xaa is absent, Gly, Ser or Cys for coupling to
      an additional peptide or protein
<220> FEATURE:
<221> NAME/KEY: MISC_FEATURE
<222> LOCATION: (4)..(4)
<223> OTHER INFORMATION: Xaa is a hydrophobic amino acid
<220> FEATURE:
<221> NAME/KEY: MISC_FEATURE
<222> LOCATION: (12)..(12)
<223> OTHER INFORMATION: Xaa is a substituted or unsubstituted Gly, Val
      or Leu
<220> FEATURE:
<221> NAME/KEY: MISC_FEATURE
<222> LOCATION: (13)..(14)
<223> OTHER INFORMATION: Xaa is absent, or Cys, Gly or Ser for coupling
      to an additional peptide or protein

<400> SEQUENCE: 5

```
Xaa Xaa Leu Xaa Thr Glu Lys Ser Arg Trp Ser Xaa Xaa Xaa
1               5                   10
```

<210> SEQ ID NO 6
<211> LENGTH: 14
<212> TYPE: PRT
<213> ORGANISM: Artificial Sequence
<220> FEATURE:
<223> OTHER INFORMATION: synthetic peptide
<220> FEATURE:
<221> NAME/KEY: MISC_FEATURE
<222> LOCATION: (1)..(2)
<223> OTHER INFORMATION: Xaa is absent or Gly, Ser or Cys for coupling
      to an additional peptide or protein
<220> FEATURE:
<221> NAME/KEY: MISC_FEATURE
<222> LOCATION: (4)..(4)
<223> OTHER INFORMATION: Xaa is a substituted or unsubstituted Ala, Ile,
      Met, or Leu,
<220> FEATURE:
<221> NAME/KEY: MISC_FEATURE
<222> LOCATION: (12)..(12)
<223> OTHER INFORMATION: Xaa is a substituted or unsubstituted Gly, Ile,
      Val or Leu.
<220> FEATURE:
<221> NAME/KEY: MISC_FEATURE
<222> LOCATION: (13)..(14)
<223> OTHER INFORMATION: Xaa is absent, Gly, Ser or Cys for coupling to
      an additional peptide or protein

<400> SEQUENCE: 6

```
Xaa Xaa Leu Xaa Thr Glu Lys Ser Arg Trp Ser Xaa Xaa Xaa
1               5                   10
```

<210> SEQ ID NO 7
<211> LENGTH: 14
<212> TYPE: PRT
<213> ORGANISM: Artificial Sequence
<220> FEATURE:
<223> OTHER INFORMATION: synthetic peptide
<220> FEATURE:
<221> NAME/KEY: MISC_FEATURE
<222> LOCATION: (1)..(2)

```
<223> OTHER INFORMATION: Xaa is absent, Gly, Ser or Cys for coupling to
      an additional peptide or protein
<220> FEATURE:
<221> NAME/KEY: MISC_FEATURE
<222> LOCATION: (13)..(14)
<223> OTHER INFORMATION: Xaa is absent, Gly, Ser or Cys for coupling to
      an additional peptide or protein

<400> SEQUENCE: 7

Xaa Xaa Leu Ile Thr Glu Lys Ser Arg Trp Ser Gly Xaa Xaa
1               5                   10

<210> SEQ ID NO 8
<211> LENGTH: 14
<212> TYPE: PRT
<213> ORGANISM: Artificial Sequence
<220> FEATURE:
<223> OTHER INFORMATION: synthetic peptide
<220> FEATURE:
<221> NAME/KEY: MISC_FEATURE
<222> LOCATION: (1)..(2)
<223> OTHER INFORMATION: Xaa is absent, Gly, Ser or Cys for coupling to
      an additional peptide or protein
<220> FEATURE:
<221> NAME/KEY: MISC_FEATURE
<222> LOCATION: (13)..(14)
<223> OTHER INFORMATION: Xaa is absent, Gly, Ser or Cys for coupling to
      an additional peptide or protein

<400> SEQUENCE: 8

Xaa Xaa Leu Ile Thr Glu Lys Ser Arg Trp Ser Val Xaa Xaa
1               5                   10

<210> SEQ ID NO 9
<211> LENGTH: 14
<212> TYPE: PRT
<213> ORGANISM: Artificial Sequence
<220> FEATURE:
<223> OTHER INFORMATION: synthetic peptide
<220> FEATURE:
<221> NAME/KEY: MISC_FEATURE
<222> LOCATION: (1)..(2)
<223> OTHER INFORMATION: Xaa is absent, Gly, Ser or Cys for coupling to
      an additional peptide or protein
<220> FEATURE:
<221> NAME/KEY: MISC_FEATURE
<222> LOCATION: (13)..(14)
<223> OTHER INFORMATION: Xaa is absent, Gly, Ser or Cys for coupling to
      an additional peptide or protein

<400> SEQUENCE: 9

Xaa Xaa Leu Leu Thr Glu Lys Ser Arg Trp Ser Val Xaa Xaa
1               5                   10

<210> SEQ ID NO 10
<211> LENGTH: 14
<212> TYPE: PRT
<213> ORGANISM: Artificial Sequence
<220> FEATURE:
<223> OTHER INFORMATION: synthetic peptide
<220> FEATURE:
<221> NAME/KEY: MISC_FEATURE
<222> LOCATION: (1)..(2)
<223> OTHER INFORMATION: Xaa is absent, Gly, Ser or Cys for coupling to
      an additional peptide or protein
<220> FEATURE:
<221> NAME/KEY: MISC_FEATURE
<222> LOCATION: (13)..(14)
<223> OTHER INFORMATION: Xaa is absent, Gly, Ser or Cys for coupling to
      an additional peptide or protein

<400> SEQUENCE: 10
```

```
Xaa Xaa Leu Ala Thr Glu Lys Ser Arg Trp Ser Ile Xaa Xaa
1               5                   10
```

<210> SEQ ID NO 11
<211> LENGTH: 14
<212> TYPE: PRT
<213> ORGANISM: Artificial Sequence
<220> FEATURE:
<223> OTHER INFORMATION: synthetic peptide
<220> FEATURE:
<221> NAME/KEY: MISC_FEATURE
<222> LOCATION: (1)..(2)
<223> OTHER INFORMATION: Xaa is absent, Gly, Ser or Cys for coupling to an additional peptide or protein
<220> FEATURE:
<221> NAME/KEY: MISC_FEATURE
<222> LOCATION: (13)..(14)
<223> OTHER INFORMATION: Xaa is absent, Gly, Ser or Cys for coupling to an additional peptide or protein

<400> SEQUENCE: 11

```
Xaa Xaa Leu Met Thr Glu Lys Ser Arg Trp Ser Gly Xaa Xaa
1               5                   10
```

<210> SEQ ID NO 12
<211> LENGTH: 14
<212> TYPE: PRT
<213> ORGANISM: Artificial Sequence
<220> FEATURE:
<223> OTHER INFORMATION: synthetic peptide
<220> FEATURE:
<221> NAME/KEY: MISC_FEATURE
<222> LOCATION: (1)..(2)
<223> OTHER INFORMATION: Xaa is absent, Gly, Ser or Cys for coupling to an additional peptide or protein
<220> FEATURE:
<221> NAME/KEY: MISC_FEATURE
<222> LOCATION: (13)..(14)
<223> OTHER INFORMATION: Xaa is absent, Gly, Ser or Cys for coupling to an additional peptide or protein

<400> SEQUENCE: 12

```
Xaa Xaa Leu Ala Thr Glu Lys Ser Arg Trp Ser Val Xaa Xaa
1               5                   10
```

<210> SEQ ID NO 13
<211> LENGTH: 14
<212> TYPE: PRT
<213> ORGANISM: Artificial Sequence
<220> FEATURE:
<223> OTHER INFORMATION: synthetic peptide
<220> FEATURE:
<221> NAME/KEY: MISC_FEATURE
<222> LOCATION: (1)..(2)
<223> OTHER INFORMATION: Xaa is absent, Gly, Ser or Cys for coupling to an additional peptide or protein
<220> FEATURE:
<221> NAME/KEY: MISC_FEATURE
<222> LOCATION: (13)..(14)
<223> OTHER INFORMATION: Xaa is absent, Gly, Ser or Cys for coupling to an additional peptide or protein

<400> SEQUENCE: 13

```
Xaa Xaa Leu Leu Thr Glu Lys Ser Arg Trp Ser Gly Xaa Xaa
1               5                   10
```

<210> SEQ ID NO 14
<211> LENGTH: 14
<212> TYPE: PRT
<213> ORGANISM: Artificial Sequence
<220> FEATURE:
<223> OTHER INFORMATION: synthetic peptide

```
<220> FEATURE:
<221> NAME/KEY: MISC_FEATURE
<222> LOCATION: (1)..(2)
<223> OTHER INFORMATION: Xaa is absent, Gly, Ser or Cys for coupling to
      an additional peptide or protein
<220> FEATURE:
<221> NAME/KEY: MISC_FEATURE
<222> LOCATION: (13)..(14)
<223> OTHER INFORMATION: Xaa is absent, Gly, Ser or Cys for coupling to
      an additional peptide or protein

<400> SEQUENCE: 14

Xaa Xaa Leu Ala Thr Glu Lys Ser Arg Trp Ser Leu Xaa Xaa
1               5                   10

<210> SEQ ID NO 15
<211> LENGTH: 15
<212> TYPE: PRT
<213> ORGANISM: Homo sapiens

<400> SEQUENCE: 15

Ser His Gln Phe Glu Gln Leu Ser Gly Ser Ile Leu Trp His Ala
1               5                   10                  15

<210> SEQ ID NO 16
<211> LENGTH: 15
<212> TYPE: PRT
<213> ORGANISM: Homo sapiens

<400> SEQUENCE: 16

Glu Asp Leu Thr Val Lys Ile Gly Asp Phe Gly Leu Ala Thr Val
1               5                   10                  15

<210> SEQ ID NO 17
<211> LENGTH: 15
<212> TYPE: PRT
<213> ORGANISM: Homo sapiens

<400> SEQUENCE: 17

Asp Leu Thr Val Lys Ile Gly Asp Phe Gly Leu Ala Thr Val Lys
1               5                   10                  15

<210> SEQ ID NO 18
<211> LENGTH: 21
<212> TYPE: PRT
<213> ORGANISM: Artificial Sequence
<220> FEATURE:
<223> OTHER INFORMATION: synthetic peptide
<220> FEATURE:
<221> NAME/KEY: MISC_FEATURE
<222> LOCATION: (13)..(13)
<223> OTHER INFORMATION: Xaa13 is a substituted or unsubstituted I when
      Xaa21 is a hydrophobic amino acid; or a hydrophobic amino acid
      when Xaa21 is a subst or unsub G, V, or L; or a subst or unsub A,
      I, M or L, when Xaa21 is a subst or unsubst G, I, V, or L
<220> FEATURE:
<221> NAME/KEY: MISC_FEATURE
<222> LOCATION: (21)..(21)
<223> OTHER INFORMATION: Xaa is a hydrophobic amino acid when Xaa13 is a
      substituted or unsubstituted I; or a subst or unsub G, V, or L
      when Xaa13 is a hydrophobic amino acid; or a subst or unsub G, I,
      V, or L, when Xaa13 is a subst or unsub A, I, M or L

<400> SEQUENCE: 18

Glu Asp Leu Thr Val Lys Ile Gly Asp Phe Gly Leu Xaa Thr Glu Lys
1               5                   10                  15

Ser Arg Trp Ser Xaa
            20
```

```
<210> SEQ ID NO 19
<211> LENGTH: 20
<212> TYPE: PRT
<213> ORGANISM: Artificial Sequence
<220> FEATURE:
<223> OTHER INFORMATION: synthetic peptide
<220> FEATURE:
<221> NAME/KEY: MISC_FEATURE
<222> LOCATION: (12)..(12)
<223> OTHER INFORMATION: Xaa12 is a substituted or unsubstituted I when
      Xaa20 is a hydrophobic amino acid; or a hydrophobic amino acid
      when Xaa20 is a subst or unsub G, V, or L; or a subst or unsub A,
      I, M or L, when Xaa21 is a subst or unsubst G, I, V, or L
<220> FEATURE:
<221> NAME/KEY: MISC_FEATURE
<222> LOCATION: (20)..(20)
<223> OTHER INFORMATION: Xaa 20 is a hydrophobic amino acid when Xaa12
      is a substituted or unsubstituted I; or a subst or unsub G, V, or
      L when Xaa12  is a hydrophobic amino acid; or a subst or unsub G,
      I, V, or L, when Xaa12 is a subst or unsub  A, I, M or L

<400> SEQUENCE: 19

Asp Leu Thr Val Lys Ile Gly Asp Phe Gly Leu Xaa Thr Glu Lys Ser
1               5                   10                  15

Arg Trp Ser Xaa
            20

<210> SEQ ID NO 20
<211> LENGTH: 26
<212> TYPE: PRT
<213> ORGANISM: Artificial Sequence
<220> FEATURE:
<223> OTHER INFORMATION: synthetic peptide
<220> FEATURE:
<221> NAME/KEY: MISC_FEATURE
<222> LOCATION: (2)..(2)
<223> OTHER INFORMATION: Xaa2 is a substituted or unsubstituted I when
      Xaa10 is a hydrophobic amino acid; or a hydrophobic amino acid
      when Xaa10 is a subst or unsub G, V, or L; or a subst or unsub A,
      I, M or L, when Xaa10 is a subst or unsubst G, I, V, or L
<220> FEATURE:
<221> NAME/KEY: MISC_FEATURE
<222> LOCATION: (10)..(10)
<223> OTHER INFORMATION: Xaa10 is a hydrophobic amino acid when Xaa2 is
      a substituted or unsubstituted I; or a subst or unsub G, V, or L
      when Xaa2 is a hydrophobic amino acid; or a subst or unsub G, I,
      V, or L, when Xaa2 is a subst or unsub  A, I, M or L

<400> SEQUENCE: 20

Leu Xaa Thr Glu Lys Ser Arg Trp Ser Xaa Ser His Asp Gln Phe Glu
1               5                   10                  15

Gln Leu Ser Gly Ser Ile Leu Trp Met Ala
            20                  25

<210> SEQ ID NO 21
<211> LENGTH: 2403
<212> TYPE: DNA
<213> ORGANISM: Homo sapiens

<400> SEQUENCE: 21
atggcggcgc tgagcggtgg cggtggtggc ggcgcggagc cgggccaggc tctgttcaac     60
ggggacatgg agcccgaggc cggcgccggc gccggcgccg cggcctcttc ggctgcggac    120
cctgccattc cggaggaggt gtggaatatc aaacaaatga ttaagttgac acaggaacat    180
atagaggccc tattggacaa atttggtggg agcataatc accatcaat atatctggag     240 gcctatgaag aatacaccag caagctagat gcactccaac aaagagaaca acagttattg    300
gaatctctgg ggaacggaac tgattttttct gtttctagct ctgcatcaat ggataccgtt    360
```

-continued

```
acatcttctt cctcttctag cctttcagtg ctaccttcat ctctttcagt ttttcaaaat    420
cccacagatg tggcacggag caaccccaag tcaccacaaa aacctatcgt tagagtcttc    480
ctgcccaaca aacagaggac agtggtacct gcaaggtgtg gagttacagt ccgagacagt    540
ctaaagaaag cactgatgat gagaggtcta atcccagagt gctgtgctgt ttacagaatt    600
caggatggag agaagaaacc aattggttgg gacactgata tttcctggct tactggagaa    660
gaattgcatg tggaagtgtt ggagaatgtt ccacttacaa cacacaactt tgtacgaaaa    720 acgttttca ccttagcatt ttgtgacttt tgtcgaaagc tgcttttcca gggtttccgc      780
tgtcaaacat gtggttataa atttcaccag cgttgtagta cagaagttcc actgatgtgt    840
gttaattatg accaacttga tttgctgttt gtctccaagt tctttgaaca ccacccaata    900
ccacaggaag aggcgtcctt agcagagact gccctaacat ctggatcatc ccttccgca     960 cccgcctcgg actctattgg gccccaaatt ctcaccagtc cgtctccttc aaaatccatt   1020
ccaattccac agcccttccg accagcagat gaagatcatc gaaatcaatt tgggcaacga   1080
gaccgatcct catcagctcc caatgtgcat ataaacacaa tagaacctgt caatattgat   1140
gacttgatta gagaccaagg atttcgtggt gatggaggat caaccacagg tttgtctgct   1200 acccccctg cctcattacc tggctcacta actaacgtga aagccttaca gaaatctcca     1260
ggacctcagc gagaaaggaa gtcatcttca tcctcagaag acaggaatcg aatgaaaaca   1320
cttggtagac gggactcgag tgatgattgg gagattcctg atgggcagat tacagtggga   1380
caaagaattg gatctggatc atttggaaca gtctacaagg gaaagtggca tggtgatgtg   1440
gcagtgaaaa tgttgaatgt gacagcacct acacctcagc agttacaagc cttcaaaaat   1500
gaagtaggag tactcaggaa aacacgacat gtgaatatcc tactcttcat gggctattcc   1560
acaaagccac aactggctat tgttacccag tggtgtgagg gctccagctt gtatcaccat   1620
ctccatatca ttgagaccaa atttgagatg atcaaactta tagatattgc acgacagact   1680
gcacagggca tggattactt acacgccaag tcaatcatcc acagagacct caagagtaat   1740
aatatatttc ttcatgaaga cctcacagta aaaataggtg attttggtct agctacagag   1800
aaatctcgat ggagtgggtc ccatcagttt gaacagttgt ctggatccat tttgtggatg   1860
gcaccgaaag tcatcagaat gcaagataaa aatccataca gctttcagtc agatgtatat   1920
gcatttggaa ttgttctgta tgaattgatg actggacagt taccttattc aaacatcaac   1980
aacagggacc agataatttt tatggtggga cgaggatacc tgtctccaga tctcagtaag   2040
gtacggagta actgtccaaa agccatgaag agattaatgg cagagtgcct caaaagaaa    2100 agagatgaga gaccactctt tccccaaatt ctcgcctcta ttgagctgct ggcccgctca   2160
ttgccaaaaa ttcaccgcag tgcatcagaa ccctccttga atcgggctgg tttccaaaca   2220
gaggatttta gtctatatgc ttgtgcttct ccaaaaacac ccatccaggc agggggatat   2280
ggtgcgtttc ctgtccacgg aaagggcgaa ttcgttttcg agtctagagg gcccttcgaa   2340
caaaaactca tctcagaaga ggatctgaat atgcataccg gtcatcatca ccatcaccat   2400
tga                                                                  2403
```

<210> SEQ ID NO 22
<211> LENGTH: 9
<212> TYPE: PRT
<213> ORGANISM: Artificial Sequence
<220> FEATURE:
<223> OTHER INFORMATION: synthetic peptide

```
<400> SEQUENCE: 22

Leu Ala Thr Glu Lys Ser Arg Trp Ser
1               5

<210> SEQ ID NO 23
<211> LENGTH: 10
<212> TYPE: PRT
<213> ORGANISM: Artificial Sequence
<220> FEATURE:
<223> OTHER INFORMATION: synthetic peptide

<400> SEQUENCE: 23

Leu Ile Thr Glu Lys Ser Arg Trp Ser Gly
1               5                   10

<210> SEQ ID NO 24
<211> LENGTH: 10
<212> TYPE: PRT
<213> ORGANISM: Artificial Sequence
<220> FEATURE:
<223> OTHER INFORMATION: synthetic peptide

<400> SEQUENCE: 24

Leu Met Thr Glu Lys Ser Arg Trp Ser Gly
1               5                   10

<210> SEQ ID NO 25
<211> LENGTH: 10
<212> TYPE: PRT
<213> ORGANISM: Artificial Sequence
<220> FEATURE:
<223> OTHER INFORMATION: synthetic peptide

<400> SEQUENCE: 25

Leu Leu Thr Glu Lys Ser Arg Trp Ser Gly
1               5                   10

<210> SEQ ID NO 26
<211> LENGTH: 10
<212> TYPE: PRT
<213> ORGANISM: Artificial Sequence
<220> FEATURE:
<223> OTHER INFORMATION: synthetic peptide

<400> SEQUENCE: 26

Leu Leu Thr Glu Lys Ser Arg Trp Ser Val
1               5                   10

<210> SEQ ID NO 27
<211> LENGTH: 10
<212> TYPE: PRT
<213> ORGANISM: Artificial Sequence
<220> FEATURE:
<223> OTHER INFORMATION: synthetic peptide

<400> SEQUENCE: 27

Leu Ala Thr Glu Lys Ser Arg Trp Ser Ile
1               5                   10

<210> SEQ ID NO 28
<211> LENGTH: 10
<212> TYPE: PRT
<213> ORGANISM: Artificial Sequence
<220> FEATURE:
<223> OTHER INFORMATION: synthetic peptide

<400> SEQUENCE: 28
```

```
Leu Ala Thr Glu Lys Ser Arg Trp Ser Leu
1               5                   10

<210> SEQ ID NO 29
<211> LENGTH: 10
<212> TYPE: PRT
<213> ORGANISM: Artificial Sequence
<220> FEATURE:
<223> OTHER INFORMATION: synthetic peptide

<400> SEQUENCE: 29

Leu Ala Thr Glu Lys Ser Arg Trp Ser Val
1               5                   10

<210> SEQ ID NO 30
<211> LENGTH: 11
<212> TYPE: PRT
<213> ORGANISM: Artificial Sequence
<220> FEATURE:
<223> OTHER INFORMATION: synthetic peptide

<400> SEQUENCE: 30

Ser Glu Glu Arg Phe Glu Ile Phe Pro Lys Glu
1               5                   10

<210> SEQ ID NO 31
<211> LENGTH: 9
<212> TYPE: PRT
<213> ORGANISM: Artificial Sequence
<220> FEATURE:
<223> OTHER INFORMATION: synthetic peptide

<400> SEQUENCE: 31

Asn Leu Val Pro Met Val Ala Thr Val
1               5

<210> SEQ ID NO 32
<211> LENGTH: 26
<212> TYPE: PRT
<213> ORGANISM: Artificial Sequence
<220> FEATURE:
<223> OTHER INFORMATION: synthetic peptide

<400> SEQUENCE: 32

Leu Ala Thr Glu Lys Ser Arg Trp Ser Gly Ser His Gln Phe Glu Gln
1               5                   10                  15

Leu Ser Gly Ser Ile Leu Trp Met Ala Pro
            20                  25

<210> SEQ ID NO 33
<211> LENGTH: 20
<212> TYPE: PRT
<213> ORGANISM: Artificial Sequence
<220> FEATURE:
<223> OTHER INFORMATION: synthetic peptide

<400> SEQUENCE: 33

Leu Thr Val Lys Ile Gly Asp Phe Gly Leu Ala Thr Glu Lys Ser Arg
1               5                   10                  15

Trp Ser Gly Ser
            20

<210> SEQ ID NO 34
<211> LENGTH: 19
<212> TYPE: PRT
```

```
<213> ORGANISM: Artificial Sequence
<220> FEATURE:
<223> OTHER INFORMATION: synthetic peptide

<400> SEQUENCE: 34

Thr Val Lys Ile Gly Asp Phe Gly Leu Ala Thr Glu Lys Ser Arg Trp
1               5                   10                  15

Ser Gly Ser
```

METHODS AND COMPOSITIONS FOR TREATING MELANOMA

CROSS-REFERENCE TO RELATED APPLICATIONS

This application is a national stage of International Patent Application No PCT/US2017/018051, filed Feb. 16, 2017, which claims the benefit of the priority of U.S. Provisional Patent Application No. 62/296,705, filed Feb. 18, 2016, which applications are incorporated herein by reference.

STATEMENT OF GOVERNMENT INTEREST

This invention was made with government support under Grant Nos. P01 CA114046 and P30 CA010815 awarded by the National Institutes of Health. The government has certain rights in the invention.

INCORPORATION-BY-REFERENCE OF MATERIAL SUBMITTED IN ELECTRONIC FORM

Applicant hereby incorporates by reference the Sequence Listing material filed in electronic form herewith. This file is labeled "WST163US-371_ST25.txt" and dated Aug. 4, 2021 with a size of 23.8 KB.

BACKGROUND OF THE INVENTION

BRAF is an intracellular signaling protein expressing frequently in melanomas for which alleles were identified as somatic mutations in 70% of melanomas, the majority of all types of nevi, and a minority of other cancers including lung, colon and ovary carcinomas, but not in normal cells. The BRAF mutations were located in exons 11 or 15, with $BRAF_{V600E}$ representing nearly all (92%) the BRAF alleles in melanoma. $BRAF_{V600E}$ has oncogenic activity through activation of the MAP kinase pathway.

Certain $BRAF_{V600E}$ based peptides that induce MHC Class I, HLA-A2-dependent cytotoxic T cell responses were identified in U.S. Pat. No. 7,811,993, which is incorporated herein by reference. These $BRAF_{V600E}$ based peptides were designed based on the amino acids 597 to 606 of the $BRAF_{V600E}$ sequence (SEQ ID NO: 1) for use in prophylactic and therapeutic treatments for melanoma. More specifically, the compositions described therein were useful in inducing responses that were not patient-specific, but that were specific for a mutation that occurs in about 70% of all melanoma patients.

There nevertheless remains a need in the art for additional pharmaceutical compositions and methods useful for treatment, prevention and diagnosis of melanoma in a large majority of patients.

SUMMARY OF THE INVENTION

In one aspect, a composition comprises a $BRAF_{V600E}$ based peptide that induces MHC Class I, HLA-A2-dependent cytotoxic T cell responses peptide or a pharmaceutically acceptable salt thereof. In one embodiment, this composition comprises peptides of the Formula II, III or IV as described herein.

In another aspect, a composition comprises a $BRAF_{V600E}$ based peptide, including a peptide of Formula I, II, III or IV described below that induces MHC Class I, HLA-A2-dependent cytotoxic T cell responses and a T helper peptide.

In another aspect, the compositions recited herein further comprise an antibody that binds a checkpoint inhibitor or a molecule that mimics the function of a checkpoint inhibitor.

In one aspect, a composition comprises a nucleic acid sequence encoding a $BRAF_{V600E}$ based peptide of Formula II, III or IV as described below.

In another aspect, a composition comprises a nucleic acid sequence encoding a $BRAF_{V600E}$ based peptide of Formula I, II, III or IV below that induces MHC Class I, HLA-A2-dependent cytotoxic T cell responses and a nucleic acid sequence encoding a T helper sequence.

In another aspect, the nucleic acid sequence-containing compositions recited herein further comprise a nucleic acid sequence encoding a checkpoint inhibitor or an antibody that binds a checkpoint inhibitor or a molecule that mimics the function of a checkpoint inhibitor.

In another aspect, a composition comprises a recombinant dendritic cell that is pretreated ex vivo with a composition containing a $BRAF_{V600E}$ based peptide, an optional T helper peptide and/or an optional antibody that binds a checkpoint inhibitor or an optional molecule that mimics the function of a checkpoint inhibitor as described herein.

In another aspect, a recombinant dendritic cell pretreated ex vivo with a composition containing a nucleic acid sequence encoding a $BRAF_{V600E}$ based peptide, optionally including a nucleic acid sequence encoding a T helper peptide and/or an antibody that binds a checkpoint inhibitor or a molecule that mimics the function of a checkpoint inhibitor as described herein.

In another aspect, a composition comprises the pretreated dendritic cell described herein with an antibody that binds a checkpoint inhibitor in a formulation suitable for simultaneous administration.

In a further aspect, a composition as described herein for use in the treatment or prophylaxis of melanoma in a mammalian subject is provided.

In another aspect, a method of treating or retarding or preventing the development of cancer, particularly melanoma, in a mammalian subject comprises administering to said subject one or more of the compositions as described herein.

Other aspects and advantages of these compositions and methods are described further in the following detailed description of the preferred embodiments thereof.

DETAILED DESCRIPTION

Figure 1:
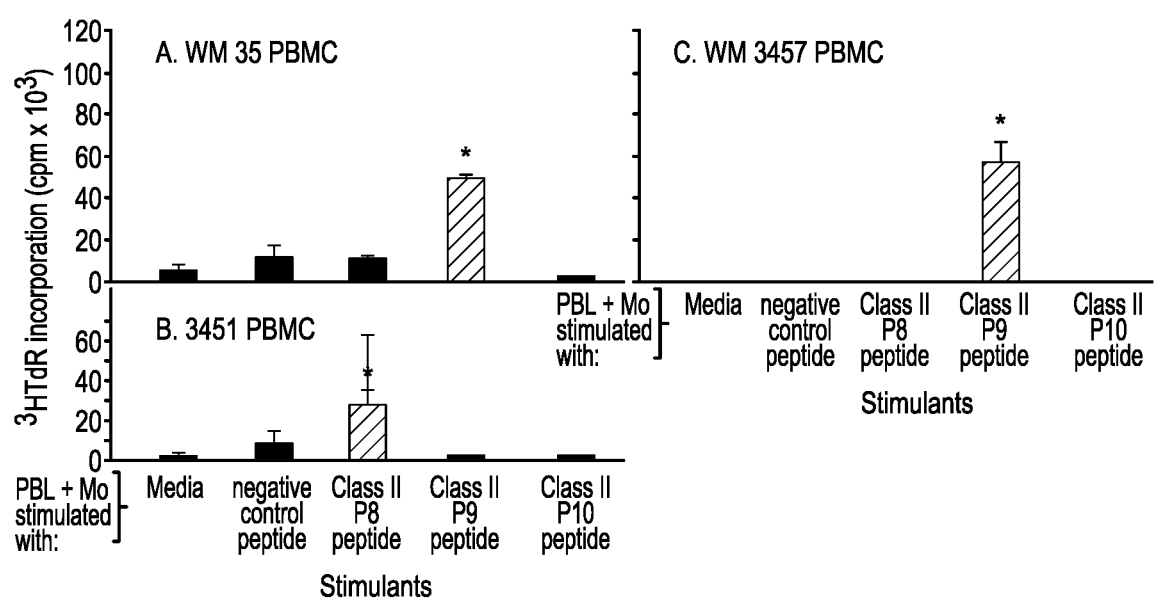
FIG. 1 shows three graphs of results of proliferative assays for three different melanoma peripheral blood mononuclear cell (PBMC) samples labeled WM35, WM3457 and 3451 with peptides derived from the $BRAF_{V600E}$ sequence. The peptides were screened for T-helper sequences (Th): Peptide P8 is amino acids residues 608-622 of BRAF, i.e., SHQFEQLSGSILWHA (SEQ ID NO: 15). Peptide P9 is amino acids residues 546-600 of BRAF, i.e., EDLTVKIGDFGLATV (SEQ ID NO: 16). Peptide P10 is amino acids residues 547-601 of BRAF, i.e., DLTVKIGDFGLATVK (SEQ ID NO: 17). These peptides bind to HLA-DR alleles using computer algorithms, as disclosed in Example 1 below. Proliferative responses were determined by standard $^3$HTdR incorporation assay. Data are expressed as mean cpm (triplicate determinations) plus SD (bar) of $^3$HTdR incorporation. *Values are significantly (p<0.01) different from the value obtained with the control peptide. This figure demonstrates that T helper peptides can induce proliferative response in melanoma patients PBMCs.

Compositions and methods are described herein that provide alternative and enhanced methods of treatment of melanoma and other cancers by the use of certain BRAF$_{V600E}$ based peptides, compositions containing the peptides and nucleic acid compositions encoding these peptides.

Certain components and definitions used in the description of these compositions and methods are defined below.

As used herein the term BRAF$_{V600E}$ refers to the human amino acid sequence of SEQ ID NO: 1 in which the amino acid residue at 600 is changed from the Val residue in the native sequence to a Glu. The nucleic acid sequence encoding BRAF$_{V600E}$ appears in SEQ ID NO: 21. In one embodiment, the nucleic acid sequence encoding amino acids 595 to 620 of SEQ ID NO: 1 was most often employed to make the changes from the native sequence to produce the peptides or nucleic acid compositions described herein. Native human BRAF amino acid and encoding nucleic acid sequences are shown in the publicly available NCBI database under Accession No. NM_004333.4. Other published sequences are available from NCBI or GenBank databases As used herein, the term "BRAF$_{V600E}$ based peptides" or "BRAF$_{V600E}$ based CTL peptides" refers to peptides based on amino acids 597-606 of BRAF$_{V600E}$ sequence, namely Leu-Ala-Thr-Glu-Lys-Ser-Arg-Trp-Ser-Gly (SEQ ID NO: 2) that induce MHC Class I, HLA-A2-dependent cytotoxic T cell responses. In one embodiment, such peptides included in this definition are the peptides identified in U.S. Pat. No. 7,811,993, incorporated by reference herein. Such peptides are defined by the Formula I::Xaa1-Xaa2-Leu-Xaa4-Xaa5-Glu-Xaa7-Xaa8-Xaa9-Trp-Xaa11-Xaa12-Xaa13-Xaa14 (SEQ ID NO: 3), or a pharmaceutically acceptable salt thereof, wherein Xaa4 is an a substituted or unsubstituted Ala, Leu, Met, Val, Pro and Gly; Xaa5 is a substituted or unsubstituted Thr and Ser; Xaa7 is a substituted or unsubstituted Lys, Arg and His; Xaa 8 is a substituted or unsubstituted Ser and Thr; Xaa9 is a substituted or unsubstituted Arg, Lys, and His; Xaa11 is a substituted or unsubstituted Thr, Val, Leu and Ser; Xaa12 is absent or is a substituted or unsubstituted Gly, Pro or Leu.

Also included in this definition of BRAF$_{V600E}$ based peptides are the peptides defined by Formulae II, III and IV. Formula II is Xaa1-Xaa2-Leu-Xaa4-Thr-Glu-Lys-Ser-Arg-Trp-Ser-Xaa12-Xaa13-Xaa14 (SEQ ID NO:4), wherein Xaa4 is a substituted or unsubstituted Ile, and Xaa12 is a hydrophobic residue. Formula III is Xaa1-Xaa2-Leu-Xaa4-Thr-Glu-Lys-Ser-Arg-Trp-Ser-Xaa12-Xaa13-Xaa14 (SEQ ID NO: 5), wherein Xaa4 is a hydrophobic residue and Xaa12 is a substituted or unsubstituted Gly, Val or Leu. Formula IV is Xaa1-Xaa2-Leu-Xaa4-Thr-Glu-Lys-Ser-Arg-Trp-Ser-Xaa12-Xaa13-Xaa14 (SEQ ID NO: 6), wherein Xaa4 is a substituted or unsubstituted Ala, Ile, Met, or Leu, and wherein Xaa12 is a substituted or unsubstituted Gly, Ile, Val or Leu.

Also, according to Formula I, II, III or IV, in all peptides of each formula, Xaa1, Xaa2 and Xaa13, Xaa14 are each independently absent or provide a spacer for coupling of a peptide of each formula to a second peptide or protein at the N- or C-termini of the peptide. Such spacers may be amino acid sequences or chemical compounds ordinarily used as spacers. For example, in one embodiment, Xaa1 is absent and Xaa2 is a Cys; in another embodiment, Xaa1-Xaa2 is Gly-Ser. In another embodiment Xaa13 is a Cys; Xaa14 is absent. In still another embodiment, Xaa13-Xaa14 is Gly-Ser. In still further embodiments, Xaa1-Xaa2 and Xaa13-Xaa14 are identical. In another embodiment, Xaa1-Xaa2 and Xaa13-Xaa14 are different. In another embodiment of a peptide of Formula II, III or IV, Xaa1-Xaa2 and Xaa13-Xaa14 are independently absent, or Xaa1-Xaa2 are absent-Cys and Xaa13-Xaa14 are absent-Cys for coupling to an additional peptide or protein.

By "hydrophobic residue" is meant a substituted or unsubstituted amino acid which imparts hydrophobicity to the resulting BRAF$_{V600E}$-based peptide. Unsubstituted amino acids having hydrophobic side chains are glycine (Gly), alanine (Ala), valine (Val), leucine (Leu), isoleucine (Ile), proline (Pro), phenylalanine (Phe), methionine (Met), and tryptophan (Trp). Various substitutions or modifications to the amino acids may make then more or less hydrophobic.

Examples of specific BRAF$_{V600E}$ based peptides of Formula I through IV include, among other sequences:

```
                                            (SEQ ID NO: 7)
Xaa1-Xaa2-Leu-Ile-Thr-Glu-Lys-Ser-Arg-Trp-Ser-
Gly-Xaa13-Xaa14;

(SEQ ID NO: 8)
Xaa1-Xaa2-Leu-Ile-Thr-Glu-Lys-Ser-Arg-Trp-Ser-
Val-Xaa13-Xaa14;

(SEQ ID NO: 9)
Xaa1-Xaa2-Leu-Leu-Thr-Glu-Lys-Ser-Arg-Trp-Ser-
Val-Xaa13-Xaa14;

(SEQ ID NO: 10)
Xaa1-Xaa2-Leu-Ala-Thr-Glu-Lys-Ser-Arg-Trp-Ser-
Ile-Xaa13-Xaa14;
```

-continued

```
                                              (SEQ ID NO: 11)
Xaa1-Xaa2-Leu-Met-Thr-Glu-Lys-Ser-Arg-Trp-Ser-
Gly-Xaa13-Xaa14, (SEQ ID NO: 12)
Xaa1-Xaa2-Leu-Ala-Thr-Glu-Lys-Ser-Arg-Trp-Ser-
Val-Xaa13-Xaa14;

(SEQ ID NO: 13)
Xaa1-Xaa2-Leu-Leu-Thr-Glu-Lys-Ser-Arg-Trp-Ser-
Gly-Xaa13-Xaa14; and (SEQ ID NO: 14)
Xaa1-Xaa2-Leu-Ala-Thr-Glu-Lys-Ser-Arg-Trp-Ser-
Leu-Xaa13-Xaa14.
```

By "T helper peptide" or "T helper sequence" or "Th peptide" as used herein is meant certain T helper sequences, or modified variants thereof of BRAF$_{V600E}$ SEQ ID NO: 1, namely, amino acids 607-621, 588 to 600 and 589 to 601 of SEQ ID NO: 1. In one embodiment, a suitable Th peptide is Ser-His-Gln-Phe-Glu-Gln-Leu-Ser-Gly-Ser-Ile-Leu-Trp-His-Ala (SEQ ID NO: 15), which spans amino acid 607 to 622 of BRAF$_{V600E}$. In another embodiment, a suitable Th peptide is Glu-Asp-Leu-Thr-Val-Lys-Ile-Gly-Asp-Phe-Gly-Leu-Ala-Thr-Val (SEQ ID NO: 16), which spans amino acid 588 to 600 of BRAF$_{V600E}$. In another embodiment, a suitable Th peptide is Asp-Leu-Thr-Val-Lys-Ile-Gly-Asp-Phe-Gly-Leu-Ala-Thr-Val-Lys (SEQ ID NO: 17), which spans amino acid 589 to 601 of BRAF$_{V600E}$. This definition of suitable Th sequences also includes modified versions of the peptide sequences and pharmaceutically acceptable salts thereof. Peptides spanning both the T helper and BRAF$_{V600E}$ based peptides, such as spanning amino acid 597 to 622 (SEQ ID NO: 32), or amino acid 588 to 607 (SEQ ID NO: 33) or amino acid 589 to 607 (SEQ ID NO: 34), or other sequences derived from the BRAF$_{V600E}$ sequence are also possible. The definitions of BRAF$_{V600E}$ based peptides and T helper peptides also include modified versions of the peptide sequences and pharmaceutically acceptable salts thereof.

By "modified" peptides of the above Formulae I-IV is meant homologous or analogous modified sequences, wherein non-variable amino acids may be conservatively replaced individually by amino acid residues having similar characteristics. In one embodiment, the non-variable amino acid residues may be replaced by other amino acid residues bearing the same charge and/or similar side chain lengths. Similarly the non-variable naturally-occurring amino acids may be replaced by non-naturally occurring amino acid residues. For peptides of the formulae above, an amino acid residue may be a naturally-occurring amino acids, meaning one of the twenty amino acids that occur in nature in L form, which include alanine, cysteine, aspartate, glutamate, phenylalanine, glycine, histidine, isoleucine, lysine, leucine, methionine, asparagine, proline, glutamine, arginine, serine, threonine, valine, tryptophan, and tyrosine, or any derivative thereof produced through a naturally-occurring biological process or pathway.

Also encompassed by the term "modifications" of the Formulae I-IV above are non-naturally-occurring amino acids. This latter term is used herein to refer to an amino acid other than a naturally-occurring amino acid as defined above, which can be synthesized or "man-made", and including a derivative thereof, whether produced synthetically or via a biological process or pathway. Non-naturally occurring amino acids include, without limitation, D amino acids, amino acids containing unnaturally substituted side chains, e.g., an N-methylated amino acid, cyclic amino acids, diamino acids, B-amino acids, homo amino acids. In some embodiments, the non-naturally occurring amino acids used in the above formulae are only those that do not strain the binding formation by adding extra atoms to the peptide backbone, because backbone hydrogen bonding contact with the MHC is desirable for these peptides. Non-naturally-occurring or unnatural amino acids may be characterized by novel backbone and side chain structures and are widely available from commercial reagent suppliers, such as Sigma-Aldrich (on the world-wide web at sigmaaldrich.com), on the world-wide web at Netchem.com, and other sites. Such non-naturally occurring amino acid(s) when employed in the peptides and compositions herein are anticipated to make the compounds more resistant to degradation by mammalian enzymes in serum, saliva, stomach and intestines, and thus compounds that are composed of one or more such amino acids may confer upon the compound enhanced stability and bioavailability in vivo. A variety of methods for producing non-natural amino acids are known and may be selected by one of skill in the art.

In one embodiment, a class of non-naturally occurring amino acids includes L amino acids that effect stereochemistry. Thus, in one embodiment of compounds, one or more of the amino acids in the peptide may be in L form, while others may be in D form. Another non-naturally occurring amino acid is an amino acid which is modified to contain a substitution on the alpha-carbon in the amino acid structure. For example, the alpha-carbon may be substituted by a suitable hydrocarbon moiety, such as aminoisobutyrate. Still another class of non-naturally occurring amino acids is amino acids which are modified or mutated to extend their carbon chain length. For example, an amino acid with a single alpha-carbon chain, may be extended with at least one additional carbon, i.e., a beta-carbon, and so on. An additional modification to an amino acid is the insertion of a substituent on the nitrogen of the amino group. An example of this type of modification is an N-methyl amino acid. The addition of substituents on the alpha carbon or additional carbons or on the nitrogen of the amino acid molecule may occur in any of the amino acids of the formulae above.

Among useful substituents for creating the non-naturally occurring amino acids are straight chain, branched, cyclic or heterocyclic $C_{1-12}$ alkyl groups, and straight chain, branched, cyclic, or heterocyclic $C_{1-12}$ alkanoyl groups. The amino acid may be also modified by the insertion of modifying sugars, imide groups and the like. Other amino acids are substituted in the ortho or meta position by a substituent such as H, OH, $CH_3$, halogen, $OCH_3$, $NH_2$, CH or $NO_2$.

A non-exclusive list of modified or non-naturally occurring amino acids for inclusion in compounds fitting the formulae above include amino acids modified by N-terminal acetylation, C-terminal amidation, formylation of the N-terminal methionine, gamma-carboxyglutamic acid hydroxylation of Asp, Asn, Pro or Lys residues in the compound, methylation of Lys or Arg, preferably; phosphorylation of Ser, Thr, Tyr, Asp or His in the compound, use of a pyrrolidone carboxylic acid, which is an N-terminal glutamate which has formed an internal cyclic lactam, sulphonation of Tyr, generally. Still other modifications of non-naturally occurring amino acids include use of or substitution with the following moieties: a 2-aminoadipic acid group, a 3-aminoadipic acid group, beta-Ala or beta-aminopropionic acid group, 2-aminobutryic acid, 4-aminobutyric acid, piperidinic acid, 6-aminocaproic acid, 2-aminoheptanoic acid, 2-aminoisobutryic acid, 3-aminoisobutyric acid, 2-aminopimelic acid, 2, 4 diaminobutyric acid, desmosine, 2,2'-diaminopimelic acid, 2,3-diaminopropionic acid, N-ethylglycine, N-ethylglycine, N-ethyl asparagine, hydroxylysine, allo-hydroxylysine, 3-hydroxyproline, 4-hydroxyproline, isodesmosine, allo-isoleucine, N-methylglycine, sarcosine, N-methylisoleucine, 6-N-methyllysine, N-methylvaline, 6-N-methyllysine, norvaline, norleucine, and ornithine.

Still other modifications of peptides of Formulae I-IV include fusions into polypeptides or other multimeric constructs or compositions, when either Xaa1-Xaa2 or Xaa13-Xaa14 are each absent or optional amino acids (e.g., Cys, -Gly-Ser-) or other amino acid or chemical compound spacers may be included at the N- or C-termini of the peptide for the purpose of linking two or more of the same or different $BRAF_{V600E}$-based peptides together or linking a peptide to a second peptide, such as one of the Th peptides or to a carrier. Preferably, the spacer of Xaa1-Xaa2 or Xaa13-Xaa14 is a proteolytically sensitive spacer to permit cleavage of the epitope before it enters the cell compartment where it associates with MHC. In one embodiment multiple copies of the same $BRAF_{V600E}$-based peptides are linked sequentially and expressed as a recombinantly or synthetically produced polypeptide. In one embodiment, multiple different $BRAF_{V600E}$-based peptides are linked sequentially, with and without spacer amino acids therebetween, to form a larger recombinant or synthetic fused polypeptide. In one embodiment, at least 2, 3, 4, 5, 6, 7, 8, 9, or 10 repeating units of the same $BRAF_{V600E}$-based peptide forms a polypeptide. In another embodiment, at least 2, 3, 4, 5, 6, 7, 8, 9, or 10 repeating units of the same fusion peptide, i.e., a $BRAF_{V600E}$-based peptide-T helper peptide fusion. In still a further embodiment, multiple $BRAF_{V600E}$-based peptides of fusion peptides as described are coupled to a carrier. Such peptides and multimeric compositions may be produced synthetically or recombinantly by conventional methods. In one embodiment, the peptides are prepared conventionally by known chemical synthesis techniques.

By "carrier" is meant a protein, peptide or other substrate that may enhance stability or delivery, improve the production, or change the activity spectrum of the peptide. As a few well-known examples, such carriers may be human albumin, keyhole limpet hemocyanin, polyethylene glycol, other biopolymers or other naturally or non-naturally occurring polymers. In one embodiment, the moiety is desirably a protein or other molecule which can enhance the stability of the peptide or enhance its penetration into the targeted cell. Still other proteins or peptides to which the $BRAF_{V600E}$-based peptides described herein may be linked via the spacer include keyhole limpet hemocyanin or additional MHC molecules. Still other carriers include a live antigen-presenting cell, such as a dendritic cell, which presents the peptides described herein. Still alternative carriers or peptide-carrier constructs utilize lipopeptides.

By the term "nucleic acid sequence that encodes a $BRAF_{V600E}$-based peptide" as used herein is meant an RNA or DNA sequence encoding the amino acid sequence of a $BRAF_{V600E}$-based peptide as described herein, such as a peptide of any of Formula I through IV. SEQ ID NO: 21 provides the DNA sequence of $BRAF_{V600E}$ from which other modified nucleic acid sequences can be obtained, e.g., encoding the modified peptides or fusion peptides described herein. By "nucleic acid sequence that encodes a T helper sequence" as used herein is meant an RNA or DNA sequence encoding the amino acid sequence of T helper as described herein, such as those of SEQ ID Nos: 15, 16 and 17, among others. Nucleic acid sequences may also encode polypeptide or fusions of the referenced peptides. The nucleic acid sequences may be generated and/or modified by conventional techniques and useful in prophylactic, diagnostic, and therapeutic compositions and methods designed for delivery of the nucleic acid in vivo and expression of the peptide in vivo. Nucleic acid sequences encoding the peptides described herein may be prepared by known recombinant DNA techniques and used to clone and express the peptides within a host microorganism or cell. Such nucleic acid sequences may also encode different or preferred codons for the peptide described.

Alternatively, such nucleic acid sequences encoding these peptides may be designed to incorporate other nucleic acid sequences necessary for delivery to a subject, e.g., as naked DNA or other DNA vaccine forms. For example, a suitable plasmid may be constructed containing a nucleic acid sequence encoding the selected $BRAF_{V600E}$-based peptide or T helper peptide, or both, under the control of regulatory sequences directing expression thereof in a mammalian or vertebrate cell. The components of the plasmid itself are conventional. Still other nucleic acid constructs and vectors of viral and bacterial origin, may be employed. See, e.g., U.S. Pat. No. 7,811,993, incorporated by reference herein.

As used herein, the term "checkpoint inhibitor" refers to a composition or composition in the form of an antibody or a small molecule that binds or inhibits various checkpoint proteins. Such checkpoint proteins, include, without limitation, programmed cell death protein 1 (PD-1), Programmed death-ligand 1 (PD-L1), cytotoxic T-lymphocyte-associated protein 4 (CTLA-4), B and T lymphocyte attenuator (BTLA) and Cluster of Differentiation 160 (CD160). As examples, known checkpoint inhibitors include the antibodies ipilimumab (Yervoy®), pembrolizumab (Keytruda®), and nivolumab (Opdivo®), among others. Other checkpoint inhibitors developed as small molecules or other checkpoint binding antibodies or antibody fragments are included in this definition.

As used herein, the term "antibody" refers to all types of immunoglobulins, including IgG, IgM, IgA, IgD, and IgE, including antibody fragments. The antibody can be monoclonal or polyclonal and can be of any species of origin, including (for example) mouse, rat, rabbit, horse, goat, sheep, camel, or human, or can be a chimeric antibody. See, e.g., Walker et al., Molec. Immunol. 26:403 (1989). The antibodies can be recombinant monoclonal antibodies produced according to known methods, see, e.g., U.S. Pat. No. 4,474,893 or 4,816,567, which are incorporated herein by reference. The antibodies can also be chemically constructed according to known methods, e.g., U.S. Pat. No. 4,676,980 which is incorporated herein by reference. See also, U.S. Pat. No. 8,613,922, which is incorporated herein by reference. An antibody includes, without limitation, a synthetic antibody, a recombinant antibody, a chimeric antibody, a humanized antibody, a human antibody, a CDR-grafted antibody, a multispecific binding construct that can bind two or more targets, a dual specific antibody, a bi-specific antibody or a multi-specific antibody, or an affinity matured antibody. Antibody fragments include without limitation antigen binding fragments such as a single antibody chain or an scFv fragment, a diabody, a single chain comprising complementary scFvs (tandem scFvs) or bispecific tandem scFvs, an Fv construct, a disulfide-linked Fv, a Fab construct, a Fab' construct, a F(ab')2 construct, an Fc construct, a monovalent or bivalent construct from which domains non-essential to monoclonal antibody function have been removed, a single-chain molecule containing one $V_L$, one $V_H$ antigen-binding domain, and one or two constant "effector" domains optionally connected by linker domains, a univalent antibody lacking a hinge region, a single domain antibody, a dual variable domain immunoglobulin (DVD-Ig) binding protein, a nanobody, a domain antibody, a vaccibody, a linear antibody; a heavy chain or light chain complementarity determining region, and multispecific antibodies formed from antibody fragments. Also included in this definition are antibody mimetics such as affibodies, i.e., a class of engineered affinity proteins, generally small (~6.5 kDa) single domain proteins that can be isolated for high affinity and specificity to any given protein target. Such antigen-binding fragments can be produced by known techniques.

The term "patient" or "subject" as used herein means a mammalian animal, including a human, a veterinary or farm animal, a domestic animal or pet, and animals normally used for clinical research. In one embodiment, the subject treated with the methods and composition is a human. In another embodiment, the subject treated with the methods and composition has a cancer. In another embodiment, the subject of these methods has melanoma.

As used herein the term "cancer" refers to or describes the physiological condition in mammals that is typically characterized by unregulated cell growth. In one embodiment, the term "cancer" means any cancer characterized by the presence of a solid tumor. In one embodiment, suitable cancers for treatment by the methods described herein, include, cancers having the presence of the $BRAF_{V600E}$ mutation. In another embodiment, suitable cancers include, without limitation, melanoma, breast cancer, lung cancer and ovarian cancer with such mutations. In another embodiment, suitable cancers include, without limitation, other forms of melanoma, brain cancer, colon/rectal cancer, lung cancer, ovarian cancer, adrenal cancer, anal cancer, bile duct cancer, bladder cancer, bone cancer, endometrial cancer, esophageal cancer, eye cancer, kidney cancer, laryngeal cancer, liver cancer, head and neck cancer, nasopharyngeal cancer, osteosarcoma, oral cancer, pancreatic cancer, prostate cancer, rhabdosarcoma, salivary gland cancer, stomach cancer, testicular cancer, thyroid cancer, vaginal cancer, lung cancer, and neuroendocrine cancer The term "tumor," as used herein, refers to all neoplastic cell growth and proliferation, whether malignant or benign, and all pre-cancerous and cancerous cells and tissues. In one embodiment, the tumor targeted by the methods is characterized by hypoxia, significant infiltration with T lymphocytes, and low glucose in the tumor microenvironment.

By "therapeutic reagent" or "regimen" is meant any type of treatment employed in the treatment of cancers with or without solid tumors, including, without limitation, chemotherapeutic pharmaceuticals, biological response modifiers, radiation, diet, vitamin therapy, hormone therapies, gene therapy, surgical resection, etc.

By "an immunotherapeutic composition" or "immunotherapeutic vaccine" is meant any composition including the $BRAF_{V600E}$-based peptides or nucleic acid sequences encoding same that stimulate the subject's immune system. Such immunotherapeutic compositions are designed to elicit a humoral (e.g., antibody) or cellular (e.g., a cytotoxic T cell or T helper) response, to the BRAF target gene product delivered by the immunogenic composition to a subject. The immunotherapeutic compositions or vaccines, as described herein, are created using known recombinant and synthetic techniques.

In one embodiment immunotherapeutic compositions useful in these methods involve presentation of the $BRAF_{V600E}$-based peptides to the subject's immune system. In another embodiment the immunotherapeutic composition used in the methods described herein is a DNA or RNA composition including a nucleic acid encoding the $BRAF_{V600E}$-based peptides. In another embodiment the $BRAF_{V600E}$-based peptides or encoding nucleic acid sequences are delivered via virus vectors, e.g., adenovirus, adeno-associated virus, lentivirus, retrovirus, poxvirus or others, or via virus-like particles (VLP). In another embodiment the immunotherapeutic composition used in the methods described herein is a monoclonal antibody or antigen-binding fragment(s) that specifically bind cancer antigens.

In another embodiment, the immunotherapeutic composition is a dendritic cell. Dendritic cell therapy involves the harvesting of autologous blood cells (monocytes) from a patient and pretreating the cells with a $BRAF_{V600E}$-based peptide (optionally with a Th peptide) ex vivo. By "pretreatment with" is meant that the autologous dendritic cell is cultured and expanded in the presence of the selected $BRAF_{V600E}$-based peptide at between about 1 to about 500 µM, to condition the dendritic cell to activate the immune system upon reinfusion into the subject. The time of pretreatment in one embodiment means the entire time of in vitro culture, which can span several hours to at least several days. In another embodiment, the time of pretreatment is minimally 24 hours of in vitro culture. Other time periods for pre-treatment with the peptides or nucleic acid components of the compositions described herein may be at least 1, 5, 10, 15, or 20 or more hours, or any intervening times between any specified number of hours stated herein. The pretreated dendritic cells are reintroduced, e.g., by i.v. injection, back to a patient in order to allow massive dendritic cell participation in optimally activating the immune system.

By "vector" is meant an entity that delivers a heterologous molecule to cells, either for therapeutic or vaccine purposes. As used herein, a vector may include any genetic element including, without limitation, naked DNA, a phage, transposon, cosmid, episome, plasmid, or a virus or bacterium. Vectors are generated using the techniques and sequences provided herein, described in the examples and in conjunction with techniques known to those of skill in the art. Such techniques include conventional cloning techniques of cDNA such as those described in texts such as Green and Sambrook, Molecular Cloning: A Laboratory Manual. $4^{th}$ Edit, Cold Spring Harbor Laboratory Press, 2012, use of overlapping oligonucleotide sequences of the *Salmonella* genomes, polymerase chain reaction, and any suitable method which provides the desired nucleotide sequence.

By the term "pharmaceutically acceptable carrier or vehicle" is meant a solution or suspension that is safe for human administration. Optionally such carriers enhance stability and/or immunogenicity. Such carriers include, for example, water, saline, buffered saline, alcohols, gum Arabic, vegetable oils, benzyl alcohols, polyethylene glycols, gelatin, carbohydrates, such as lactose, amylase or starch, magnesium stearate, talc, silicic acid, viscous paraffin, perfume oil, fatty acid monoglycerides and diglycerides, pentaerythritol fatty acid esters, hydroxymethylcellulose, polyvinylpyrrolidone, liposomes, oil in water emulsions and others. The compositions may further include a detergent to make the peptide more bioavailable, e.g., octylglucoside.

By "adjuvant" is meant a substance that enhances the immune response when administered together with an immunogen or antigen. In one embodiment, a suitable adjuvant is CPG. In another embodiment a suitable adjuvant is encapsulated PLG. Still other useful adjuvants are known, and include those listed and disclosed in U.S. Pat. No. 7,811,993, and its cited references, which are all incorporated herein by reference.

By "administering" or "route of administration" is meant delivery of the BRAF$_{V600E}$-based peptides, polypeptides, nucleic acid constructs, T helper peptides or nucleic acid constructs encoding them, or the checkpoint inhibitor or the pre-treated dendritic cells used in the methods herein, to the subject. As discussed in detail below, these methods can be independent for each component of the method. Each administration method can occur with or without a pharmaceutical carrier or excipient, or with or without another chemotherapeutic agent into the subject. Conventional and pharmaceutically acceptable routes of administration include, but are not limited to, systemic routes, such as intraperitoneal, intravenous, intradermal, subcutaneous, and other parenteral routes of administration or intratumoral or intranodal administration. In one embodiment, the route of administration is intradermal or subcutaneous for the peptide(s) and polypeptides. In another embodiment, the route of administration is intraperitoneal or intravascular for the checkpoint inhibitor antibodies. In another embodiment, the route of administration is intravascular or intravenous for delivery of the dendritic cell-based vaccine. Routes of administration may be combined, if desired. In some embodiments, the administration is repeated periodically, as discussed in detail below.

In the context of the compositions and methods described herein, reference to "one or more," "at least five," etc. of the compositions, peptides, antibodies or other components listed means any one or any and all combinations of them.

The words "comprise", "comprises", and "comprising" are to be interpreted inclusively rather than exclusively, i.e., to include other unspecified components or process steps.

The words "consist", "consisting", and its variants, are to be interpreted exclusively, rather than inclusively, i.e., to exclude components or steps not specifically recited.

As used herein, the phrase "consisting essentially of" limits the scope of a described composition or method to the specified materials or steps and those that do not materially affect the basic and novel characteristics of the described or claimed method or composition. Wherever in this specification, a method or composition is described as "comprising" certain steps or features, it is also meant to encompass embodiments of the same method or composition consisting essentially of those steps or features and/or consisting of those steps or features.

As used herein, the term "about" means a variability of 10% from the reference given, unless otherwise specified.

It is to be noted that the term "a" or "an", refers to one or more, for example, "an miRNA," is understood to represent one or more miRNAs. As such, the terms "a" (or "an"), "one or more," and "at least one" are used interchangeably herein.

Unless defined otherwise in this specification, technical and scientific terms used herein have the same meaning as commonly understood by one of ordinary skill in the art to which this invention belongs and by reference to published texts, which provide one skilled in the art with a general guide to many of the terms used in the present application.

Compositions for Use as Immunotherapeutic Vaccines

In one embodiment, a composition useful in the treatment of melanoma or other cancers comprises a peptide or a pharmaceutically acceptable salt thereof, the peptide having the Formula II: Xaa1-Xaa2-Leu-Xaa4-Thr-Glu-Lys-Ser-Arg-Trp-Ser-Xaa12-Xaa13-Xaa14 (SEQ ID NO:4). According to this formula, Xaa1-Xaa2 and Xaa13-Xaa14 are independently absent-absent or absent-Cys for coupling to an additional peptide or protein, and Xaa4 is a substituted or unsubstituted Ile and Xaa12 is a substituted or unsubstituted hydrophobic residue. In certain embodiments, a composition such as described herein includes a pharmaceutically acceptable vehicle or carrier. In certain embodiments, a composition such as described herein includes a liposome. In certain embodiments, a composition such as described herein includes an adjuvant. In certain embodiments, a composition such as described herein includes the adjuvant CPG or encapsulated PLG.

In still another embodiment, the composition further contains an antibody that binds a checkpoint inhibitor or a molecule that mimics the function of a checkpoint inhibitor. Among such checkpoint inhibitors are CTLA4, PD-1, PDL1, Lymphocyte activation gene-3 (LAG-3), Inducible Co-stimulatory molecule (ICOS), BTLA, Killer Cell Immunoglobulin-like Receptor (KIR), Tumor Necrosis Factor Superfamily Member 4 (OX40), Cluster of Differentiation 27 (CD27), CD40 Ligand (CD40L), Cluster of Differentiation 40 (CD40), T cell immunoglobulin and mucin domain-containing protein 3 (TIM3) or T cell immunoglobulin and mucin domain-containing protein 334 (T1M334).

In another embodiment, a composition useful in the treatment of melanoma or other cancers comprises a peptide or a pharmaceutically acceptable salt thereof, the peptide having the Formula III: Xaa1-Xaa2-Leu-Xaa4-Thr-Glu-Lys-Ser-Arg-Trp-Ser-Xaa12-Xaa13-Xaa14 (SEQ ID NO:5). According to this formula, Xaa1-Xaa2 and R2 Xaa13-Xaa14 are independently absent-absent or absent-Cys for coupling to an additional peptide or protein, and Xaa4 is a hydrophobic residue and Xaa12 is a substituted or unsubstituted Gly, Val or Leu. In certain embodiments, a composition such as described herein includes a pharmaceutically acceptable vehicle or carrier. In certain embodiments, a composition such as described herein includes a liposome. In certain embodiments, a composition such as described herein includes an adjuvant. In certain embodiments, a composition such as described herein includes the adjuvant CPG or encapsulated PLG. In still another embodiment, the composition further contains an antibody that binds a checkpoint inhibitor or a molecule that mimics the function of a checkpoint inhibitor. Among such checkpoint inhibitors are CTLA4, PD-1, PDL1 LAG-3, or TIM334.

In another embodiment, a composition useful in the treatment of melanoma or other cancers comprises a peptide or a pharmaceutically acceptable salt thereof, the peptide having the Formula IV: Xaa1-Xaa2-Leu-Xaa4-Thr-Glu-Lys-Ser-Arg-Trp-Ser-Xaa12-Xaa13-Xaa14 (SEQ ID NO:6). According to this formula, Xaa1-Xaa2 and Xaa13-Xaa14 are independently absent-absent or absent-Cys for coupling to an additional peptide or protein, and Xaa4 is a substituted or unsubstituted Ala, Ile, Met, or Leu, and wherein Xaa12 is a substituted or unsubstituted Gly, Ile, Val or Leu. In certain embodiments, a composition such as described herein includes a pharmaceutically acceptable vehicle or carrier. In certain embodiments, a composition such as described herein includes a liposome. In certain embodiments, a composition such as described herein includes an adjuvant. In certain embodiments, a composition such as described herein includes the adjuvant CPG or encapsulated PLG. In still another embodiment, the composition further contains an antibody that binds a checkpoint inhibitor or a molecule that mimics the function of a checkpoint inhibitor. Among such checkpoint inhibitors are CTLA4, PD-1, PDL1, LAG-3, ICOS, BTLA, KIR, OX40, CD27, CD40L, CD40, TIM3 or TIM334.

In one embodiment, a composition useful in the treatment of melanoma or other cancers comprises a peptide Xaa1-Xaa2-Leu-Ile-Thr-Glu-Lys-Ser-Arg-Trp-Ser-Gly-Xaa13-Xaa14 (SEQ ID NO: 7) or a pharmaceutically acceptable salt thereof. In certain embodiments, a composition such as described herein includes a pharmaceutically acceptable vehicle or carrier. In certain embodiments, a composition such as described herein includes a liposome. In certain embodiments, a composition such as described herein includes an adjuvant. In certain embodiments, a composition such as described herein includes the adjuvant CPG or encapsulated PLG. In still another embodiment, the composition further contains an antibody that binds a checkpoint inhibitor or a molecule that mimics the function of a checkpoint inhibitor. Among such checkpoint inhibitors are CTLA4, PD-1, PDL1, LAG-3, ICOS, BTLA, KIR, OX40, CD27, CD40L, CD40, TIM3 or TIM334.

In one embodiment, a composition useful in the treatment of melanoma or other cancers comprises a peptide Xaa1-Xaa2-Leu-Ile-Thr-Glu-Lys-Ser-Arg-Trp-Ser-Val-Xaa13-Xaa14 (SEQ ID NO:8) or a pharmaceutically acceptable salt thereof. In certain embodiments, a composition such as described herein includes a pharmaceutically acceptable vehicle or carrier. In certain embodiments, a composition such as described herein includes a liposome. In certain embodiments, a composition such as described herein includes an adjuvant. In certain embodiments, a composition such as described herein includes the adjuvant CPG or encapsulated PLG. In still another embodiment, the composition further contains an antibody that binds a checkpoint inhibitor or a molecule that mimics the function of a checkpoint inhibitor. Among such checkpoint inhibitors are CTLA4, PD-1, PDL1, LAG-3, ICOS, BTLA, KIR, OX40, CD27, CD40L, CD40, TIM3 or TIM334.

In one embodiment, a composition useful in the treatment of melanoma or other cancers comprises a peptide Xaa1-Xaa2-Leu-Leu-Thr-Glu-Lys-Ser-Arg-Trp-Ser-Val-Xaa13-Xaa14 (SEQ ID NO: 9) or a pharmaceutically acceptable salt thereof. In certain embodiments, a composition such as described herein includes a pharmaceutically acceptable vehicle or carrier. In certain embodiments, a composition such as described herein includes a liposome. In certain embodiments, a composition such as described herein includes an adjuvant. In certain embodiments, a composition such as described herein includes the adjuvant CPG or encapsulated PLG. In still another embodiment, the composition further contains an antibody that binds a checkpoint inhibitor or a molecule that mimics the function of a checkpoint inhibitor. Among such checkpoint inhibitors are CTLA4, PD-1, PDL1, LAG-3, ICOS, BTLA, KIR, OX40, CD27, CD40L, CD40, TIM3 or TIM334.

In one embodiment, a composition useful in the treatment of melanoma or other cancers comprises a peptide Xaa1-Xaa2-Leu-Ala-Thr-Glu-Lys-Ser-Arg-Trp-Ser-Ile-Xaa13-Xaa14 (SEQ ID NO: 10) or a pharmaceutically acceptable salt thereof. In certain embodiments, a composition such as described herein includes a pharmaceutically acceptable vehicle or carrier. In certain embodiments, a composition such as described herein includes a liposome. In certain embodiments, a composition such as described herein includes an adjuvant. In certain embodiments, a composition such as described herein includes the adjuvant CPG or encapsulated PLG. In still another embodiment, the composition further contains an antibody that binds a checkpoint inhibitor or a molecule that mimics the function of a checkpoint inhibitor. Among such checkpoint inhibitors are CTLA4, PD-1, PDL1, LAG-3, ICOS, BTLA, KIR, OX40, CD27, CD40L, CD40, TIM3 or TIM334.

In one embodiment, a composition useful in the treatment of melanoma or other cancers comprises a peptide Xaa1-Xaa2-Leu-Met-Thr-Glu-Lys-Ser-Arg-Trp-Ser-Gly-Xaa13-Xaa14 (SEQ ID NO: 11) or a pharmaceutically acceptable salt thereof. In certain embodiments, a composition such as described herein includes a pharmaceutically acceptable vehicle or carrier. In certain embodiments, a composition such as described herein includes a liposome. In certain embodiments, a composition such as described herein includes an adjuvant. In certain embodiments, a composition such as described herein includes the adjuvant CPG or encapsulated PLG. In still another embodiment, the composition further contains an antibody that binds a checkpoint inhibitor or a molecule that mimics the function of a checkpoint inhibitor. Among such checkpoint inhibitors are CTLA4, PD-1, PDL1, LAG-3, ICOS, BTLA, KIR, OX40, CD27, CD40L, CD40, TIM3 or TIM334.

In one embodiment, a composition useful in the treatment of melanoma or other cancers comprises a peptide Xaa1-Xaa2-Leu-Ala-Thr-Glu-Lys-Ser-Arg-Trp-Ser-Val-Xaa13-Xaa14 (SEQ ID NO: 12) or a pharmaceutically acceptable salt thereof. In certain embodiments, a composition such as described herein includes a pharmaceutically acceptable vehicle or carrier. In certain embodiments, a composition such as described herein includes a liposome. In certain embodiments, a composition such as described herein includes an adjuvant. In certain embodiments, a composition such as described herein includes the adjuvant CPG or encapsulated PLG. In still another embodiment, the composition further contains an antibody that binds a checkpoint inhibitor or a molecule that mimics the function of a checkpoint inhibitor. Among such checkpoint inhibitors are CTLA4, PD-1, PDL1, LAG-3, ICOS, BTLA, KIR, OX40, CD27, CD40L, CD40, TIM3 or TIM334.

In one embodiment, a composition useful in the treatment of melanoma or other cancers comprises a peptide Xaa1-Xaa2-Leu-Leu-Thr-Glu-Lys-Ser-Arg-Trp-Ser-Gly-Xaa13-Xaa14 (SEQ ID NO: 13) or a pharmaceutically acceptable salt thereof. In certain embodiments, a composition such as described herein includes a pharmaceutically acceptable vehicle or carrier. In certain embodiments, a composition such as described herein includes a liposome. In certain embodiments, a composition such as described herein includes an adjuvant. In certain embodiments, a composition such as described herein includes the adjuvant CPG or encapsulated PLG. In still another embodiment, the composition further contains an antibody that binds a checkpoint inhibitor or a molecule that mimics the function of a checkpoint inhibitor. Among such checkpoint inhibitors are CTLA4, PD-1, PDL1, LAG-3, ICOS, BTLA, KIR, OX40, CD27, CD40L, CD40, TIM3 or TIM334.

In one embodiment, a composition useful in the treatment of melanoma or other cancers comprises a peptide Xaa1-Xaa2-Leu-Ala-Thr-Glu-Lys-Ser-Arg-Trp-Ser-Leu-Xaa13-Xaa14 (SEQ ID NO: 14) or a pharmaceutically acceptable salt thereof. In certain embodiments, a composition such as described herein includes a pharmaceutically acceptable vehicle or carrier. In certain embodiments, a composition such as described herein includes a liposome. In certain embodiments, a composition such as described herein includes an adjuvant. In certain embodiments, a composition such as described herein includes the adjuvant CPG or encapsulated PLG. In still another embodiment, the composition further contains an antibody that binds a checkpoint inhibitor or a molecule that mimics the function of a checkpoint inhibitor. Among such checkpoint inhibitors are CTLA4, PD-1, PD-L1, LAG-3, ICOS, BTLA, KIR, OX40, CD27, CD40L, CD40, TIM3 or TIM334.

In another embodiment, a composition useful in the treatment of melanoma or other cancers comprises a peptide or a pharmaceutically acceptable salt thereof, the peptide of Formula I, II, III or IV and a T helper peptide. In one embodiment, the T cell peptide is coupled or fused at either the N- or C-termini of the peptide of the $BRAF_{V600E}$-based peptide or polypeptide. In one embodiment, the T helper peptide is Ser-His-Gln-Phe-Glu-Gln-Leu-Ser-Gly-Ser-Ile-Leu-Trp-His-Ala (SEQ ID NO: 15). In one embodiment, the T helper peptide is Glu-Asp-Leu-Thr-Val-Lys-Ile-Gly-Asp-Phe-Gly-Leu-Ala-Thr-Val (SEQ ID NO: 16). In one embodiment, the T helper peptide is Asp-Leu-Thr-Val-Lys-Ile-Gly-Asp-Phe-Gly-Leu-Ala-Thr-Val-Lys (SEQ ID NO: 17).

In yet another embodiment of a composition containing a fused $BRAF_{V600E}$-based peptide or polypeptide and a T helper sequence is the sequence spanning the Th and CTL sequences found in $BRAF_{V600E}$. In one embodiment, this sequence spans about amino acid 586 to amino acid 606 and has the formula, e.g., Glu-Asp-Leu-Thr-Val-Lys-Ile-Gly-Asp-Phe-Gly-Leu-Xaa13-Thr-Glu-Lys-Ser-Arg-Trp-Ser-Xaa21 (SEQ ID NO: 18) with Xaa13 and Xaa21 as described in the same way as Xaa4 and Xaa12, respectively, in any of Formula II, III or IV above.

In another embodiment, this sequence spans about amino acid 587 to amino acid 606 and has the formula, e.g., Asp-Leu-Thr-Val-Lys-Ile-Gly-Asp-Phe-Gly-Leu-Xaa12-Thr-Glu-Lys-Ser-Arg-Trp-Ser-Xaa20 (SEQ ID NO: 19), with Xaa12 and Xaa20 as described in the same manner as Xaa4 and Xaa12, respectively in any of Formula II, III or IV above. In still another embodiment, this sequence spans about amino acid 597 to amino acid 621 and has the formula, e.g., Leu-Xaa2-Thr-Glu-Lys-Ser-Arg-Trp-Ser-Xaa10-Ser-His-Gln-Phe-Glu-Gln-Leu-Ser-Gly-Ser-Ile-Leu-Trp-Met-Ala (SEQ ID NO: 20) with Xaa2 and Xaa10 as described for Xaa4 and Xaa12, respectively, in any of Formula II, III or IV above.

Still other embodiments of these sequences can contain modified amino acids, or replacement amino acids in the positions specified in Formula I, or conservative replacements, possible spacer amino acids on either end of the peptide, or multiple Th sequences flanking the amino- or carboxy amino acid of the whole peptide, as described above. Nucleic acid sequences encoding these sequences are also useful in these compositions.

In certain embodiments, a composition such as described herein includes a pharmaceutically acceptable vehicle or carrier. In certain embodiments, a composition such as described herein includes a liposome. In certain embodiments, a composition such as described herein includes an adjuvant. In certain embodiments, a composition such as described herein includes the adjuvant CPG or encapsulated PLG. In still another embodiment, the composition further contains an antibody that binds a checkpoint inhibitor or a molecule that mimics the function of a checkpoint inhibitor. Among such checkpoint inhibitors are CTLA4, PD-1, PDL1, LAG-3, ICOS, BTLA, KIR, OX40, CD27, CD40L, CD40, TIM3 or TIM334.

In another embodiment, a composition useful in the treatment of melanoma or other cancers comprises multiple copies of the same $BRAF_{V600E}$-based peptide or polypeptide fused or coupled together. In another embodiment, a composition useful in the treatment of melanoma or other cancers comprises multiple copies of a fused peptide, which comprises same $BRAF_{V600E}$-based peptide or polypeptide fused or coupled to a T helper peptide. In another embodiment, such compositions comprise a $BRAF_{V600E}$-based polypeptide or fusion formed from 5 to 10 of the same fused in frame or via a spacer. In still another embodiment, the composition further contains an antibody that binds a checkpoint inhibitor or a molecule that mimics the function of a checkpoint inhibitor. Among such checkpoint inhibitors are CTLA4, PD-1, PDL1, LAG-3, ICOS, BTLA, KIR, OX40, CD27, CD40L, CD40, TIM3 or TIM334.

In still further embodiments, a composition useful in the treatment of melanoma or other cancers comprises one or multiple of the $BRAF_{V600E}$-based peptide or polypeptides or fusions with T helper sequences as described herein. Any number of single peptides or multimeric constructs may be mixed together to form a single composition. The peptides may be formulated with a pharmaceutically acceptable carrier, adjuvant, diluent, other optional components, or some combination thereof. For use in such compositions, the selected peptide(s) may be produced preferably synthetically, but also recombinantly, as disclosed above. In still another embodiment, the composition further contains an antibody that binds a checkpoint inhibitor or a molecule that mimics the function of a checkpoint inhibitor. Among such checkpoint inhibitors are CTLA4, PD-1, PDL1, LAG-3, ICOS, BTLA, KIR, OX40, CD27, CD40L, CD40, TIM3 or TIM334.

In still further embodiments, a composition useful in the treatment of melanoma or other cancers comprises one or multiple of the $BRAF_{V600E}$-based peptides described herein in the form of a salt with an acid. The compounds have at least one amino/amine groups which can form salts. Where two or more amino groups are present in the compound, a formulation of mixed salts can be prepared. Acids which can be used preferably include compatible inorganic acids such as hydrochloric and organic acids (or salts thereof) more preferably those occurring in living organisms, including but not limited to oxalic acid, glucuronic acid, pyruvic acid, lactic acid, citric acid, isocitric acid-ketoglutaric acid, succinic acid, malic acid, and oxaloacetic acid. In the preferred case of an aqueous solution, the desired anion can be added either as the free acid, or a salt, preferably one which is highly soluble in water, for example the sodium or potassium salts, but also the lithium, magnesium, calcium or ammonium salts. Moreover, these salts can be used either in anhydrous or hydrated forms. For example citric acid can be used as the anhydrous free acid, the monohydrate free acid, the anhydrous trisodium salt, or the dihydrate trisodium salt. These salts can be prepared by the methods described in International Patent Publication No. WO 96/02269, incorporated by reference herein.

In still another embodiment, a composition useful in the treatment of melanoma or other cancers comprises a nucleic acid sequence, such as a DNA vaccine, encoding any of the components of the compositions containing $BRAF_{V600E}$-based peptides of Formula I, II, III or IV, or polypeptides comprising two or more copies of the $BRAF_{V600E}$-based peptides or fusions with T helper sequences described above. In one embodiment, a nucleic acid sequence for use as DNA vaccines can take the form of a recombinant vector carrying the above-described peptide-encoding nucleic acid sequence. In another embodiment, the nucleic acid sequences may be carried, and the $BRAF_{V600E}$ peptides are expressed by, plasmid based systems, of which many are commercially available or in replicating or non-replicating recombinant viral vectors. The nucleic acid sequences discussed herein may be expressed and produced using such vectors in vitro in desired host cells or in vivo in a mammalian subject. In one embodiment, the vector is a non-pathogenic virus. In another embodiment, the vector is a non-replicating virus. In one embodiment, a desirable viral vector may be a retroviral vector, such as a lentiviral vector. In another embodiment, a desirable vector is an adenoviral vector. In still another embodiment, a suitable vector is an adeno-associated viral vector. Adeno, adeno-associated and lentiviruses are generally preferred because they infect actively dividing as well as resting and differentiated cells such as the stem cells, macrophages and neurons. A variety of adenovirus, lentivirus and AAV strains are available from the American Type Culture Collection, Manassas, Va., or available by request from a variety of commercial and institutional sources. Further, the sequences of many such strains are available from a variety of databases including, e.g., PubMed and GenBank.

In one embodiment, a lentiviral vector is used. Among useful vectors are the equine infectious anemia virus and feline as well as bovine immunodeficiency virus, and HIV-based vectors. A variety of useful lentivirus vectors, as well as the methods and manipulations for generating such vectors for use in transducing cells and expressing heterologous genes, e.g., N Manjunath et al, 2009 Adv Drug Deliv Rev., 61(9): 732-745; Porter et al., N Engl J Med. 2011 Aug. 25; 365(8):725-33), among others.

In another embodiment, the vector used herein is an adenovirus vector. Such vectors can be constructed using adenovirus DNA of one or more of any of the known adenovirus serotypes. See, e.g., T. Shenk et al., Adenoviridae: The Viruses and their Replication", Ch. 67, in FIELD'S VIROLOGY, 6th Ed., edited by B. N Fields et al, (Lippincott Raven Publishers, Philadelphia, 1996), p. 111-2112; U.S. Pat. No. 6,083,716, which describes the genome of two chimpanzee adenoviruses; U.S. Pat. No. 7,247,472; WO 2005/1071093, etc. One of skill in the art can readily construct a suitable adenovirus vector to carry and express a nucleotide sequence encoding a desired BRAF$_{V600E}$ and/or T helper peptide or fusion peptides as described herein. In another embodiment, the vector used herein is an adeno-associated virus (AAV) vector. Such vectors can be constructed using AAV DNA of one or more of the known AAV serotypes. See, e.g., U.S. Pat. Nos. 7,803,611; 7,696,179, among others.

In yet another embodiment, the vector used herein is a bacterial vector. In one embodiment, the bacterial vector is *Listeria monocytogenes*. See, e.g., Lauer et al, Infect. Immunity, 76(8):3742-53 (August 2008). Thus, in one embodiment, the bacterial vector is live-attenuated or photochemically inactivated. The BRAF$_{V600E}$ and/or T helper peptide or fusion peptides as described herein can be expressed recombinantly by the bacteria, e.g., via a plasmid introduced into the bacteria, or integrated into the bacterial genome, i.e., via homologous recombination.

These vectors also include conventional control elements that permit transcription, translation and/or expression of the nucleic acid sequences in a cell transfected with the plasmid vector or infected with the viral vector. A great number of expression control sequences, including promoters which are native, constitutive, inducible and/or tissue-specific, are known in the art and may be utilized. In one embodiment, the promoter is selected based on the chosen vector. In another embodiment, when the vector is lentivirus, the promoter is U6, H1, CMV IE gene, EF-1α, ubiquitin C, or phosphoglycero-kinase (PGK) promoter. In another embodiment, when the vector is an AAV, the promoter is an RSV, U6, or CMV promoter. In another embodiment, when the vector is an adenovirus, the promoter is RSV, U6, CMV, or H1 promoters. In another embodiment, when the vector is *Listeria monocytogenes*, the promoter is a hly or actA promoter. Still other conventional expression control sequences include selectable markers or reporter genes, which may include sequences encoding geneticin, hygromicin, ampicillin or purimycin resistance, among others. Other components of the vector may include an origin of replication. Selection of these and other promoters and vector elements are conventional and many such sequences are available (see, e.g., the references cited herein).

The nucleic acid sequences encoding the BRAF$_{V600E}$ and/or T helper sequences for use in DNA vaccines are generated using the techniques and sequences provided herein, in conjunction with techniques known to those of skill in the art. Such techniques include conventional cloning techniques of cDNA such as those described in texts (Sambrook et al, Molecular Cloning: A Laboratory Manual, Cold Spring Harbor Press, Cold Spring Harbor, N.Y.), use of overlapping oligonucleotide sequences, polymerase chain reaction, the various known Crispr-Cas methodologies, and any suitable method which provides the desired nucleotide sequence.

Thus, in one embodiment, using the information taught herein and publicly available and known vector construction components and techniques, one of skill in the art can construct a viral vector (or plasmid) that expresses the desired nucleic acid sequence encoding the BRAF$_{V600E}$ and/or T helper sequences. The BRAF$_{V600E}$ and/or T helper polypeptides or proteins or fusion polypeptides or proteins encoded by these nucleic acid constructs may be expressed in vitro, or ex vivo in host cells or expressed in vivo by administration to a mammalian subject. Alternatively the BRAF$_{V600E}$ and/or T helper polypeptides or proteins or fusion polypeptides may be generated synthetically by known chemical synthesis methodologies. One of skill in the art can select the appropriate method to produce these BRAF$_{V600E}$ and/or T helper polypeptides or proteins or fusion polypeptides depending upon the components, the efficiency of the methodologies and the intended use, e.g., whether for administration as proteins, nucleic acids or in adoptive T cells, or otherwise to accomplish the desired therapeutic result.

Such nucleic acid compositions may include formulations with suitable vehicles for direct DNA, plasmid nucleic acid, or recombinant vector administration. Such vehicles include, without limitation, saline, sucrose, protamine, polybrene, polylysine, polycations, proteins, or spermidine, etc. See e.g, International Patent Publication No. WO94/01139. Other pharmaceutically acceptable vehicles, excipients and typical components of DNA compositions are optionally included in these compositions.

In still another embodiment, the composition further contains an antibody that binds a checkpoint inhibitor or a molecule that mimics the function of a checkpoint inhibitor. Among such checkpoint inhibitors are CTLA4, PD-1, PDL1, LAG-3, ICOS, BTLA, KIR, OX40, CD27, CD40L, CD40, TIM3 or TIM334.

In still another embodiment, a composition as described above is provided containing one or more of the BRAF$_{V600E}$-based peptides, polypeptides or fusions or nucleic acid sequences encoding same, including DNA vaccines, in a pharmaceutically acceptable carrier, adjuvant or diluent or a combination thereof. This composition can contain other pharmaceutically acceptable components for enhancing the penetration of the compound into a cell and/or for extending its bioavailability and increasing its resistance to enzymatic degradation in vivo. Such a composition, in one embodiment, is a pharmaceutical composition. Such a composition in another embodiment is immunogenic.

The pharmaceutical compositions, both peptide or nucleic acid compositions, may also be formulated to suit a selected route of administration, and may contain ingredients specific to the route of administration as known to one of skill in the art of pharmaceutical formulation. A non-exclusive list of auxiliary agents are lubricants, preservatives, stabilizers, wetting agents, emulsifiers, salts for influencing osmotic pressure, buffers, coloring, flavoring and/or aromatic substances and the like that do not deleteriously react with the active compounds. The preparation of these pharmaceutically acceptable compositions, from the above-described components, having appropriate pH isotonicity, stability and other conventional characteristics is within the skill of the art.

In still another embodiment, a composition useful in the treatment of melanoma or other cancers comprises a recombinant dendritic cell pretreated ex vivo with any of the $BRAF_{V600E}$-based peptides of Formula I, II, III or IV, or polypeptides comprising two or more copies of the $BRAF_{V600E}$-based peptides or fusions with T helper sequences described above. In still another embodiment, the composition further contains an antibody that binds a checkpoint inhibitor or a molecule that mimics the function of a checkpoint inhibitor. Among such checkpoint inhibitors are CTLA4, PD-1, PDL1, LAG-3, ICOS, BTLA, KIR, OX40, CD27, CD40L, CD40, TIM3 or TIM334.

In still another embodiment, useful in the treatment of melanoma or other cancers includes a modified T cell is a T cell that has been transduced or transfected with one of the above-described vectors carrying the nucleic acid constructs encoding the $BRAF_{V600E}$-based peptides, polypeptides or fusions or nucleic acid sequences encoding same. Desirably, the T cell is a primary T cell, a CD8 (cytotoxic) T cell, or an NK T cell or other T cell obtained from the same mammalian subject into whom the modified T cell is administered or from another member of the mammalian species. In one embodiment, the T cell is an autologous human T cell or natural killer (NK) T cell obtained from the subject or from a bone marrow transplant match for the subject. Other suitable T cells include T cells obtained from resected tumors, a polyclonal or monoclonal tumor-reactive T cell. The T cell is generally obtained by apheresis, and transfected or transduced with the selected nucleic acid construct to express the $BRAF_{V600E}$ peptide or fusion with a T helper protein in vivo.

Methods of Treatment

A method of treating or retarding or preventing the development of melanoma in a mammalian subject comprises administering to a subject in need thereof, i.e., a subject with melanoma, a composition of any described above. The method is useful in the treatment of melanomas to induce an MHC class I, HLA-A2 restricted CTL response by the patient against the cancer.

These therapeutic compositions and components of the methods may be administered to a patient, preferably suspended in a biologically compatible solution or pharmaceutically acceptable delivery vehicle. The various components of the methods are prepared for administration by being suspended or dissolved in a pharmaceutically or physiologically acceptable carrier such as isotonic saline; isotonic salts solution or other formulations that will be apparent to those skilled in such administration. The appropriate carrier will be evident to those skilled in the art and will depend in large part upon the route of administration. Other aqueous and non-aqueous isotonic sterile injection solutions and aqueous and non-aqueous sterile suspensions known to be pharmaceutically acceptable carriers and well known to those of skill in the art may be employed for this purpose.

A pharmaceutical composition as described above may be administered by any appropriate route, such as subcutaneous injection for the peptide compositions or intravenous injection for the checkpoint inhibitor antibody and infusion of the dendritic cells. Still other routes of administration as described above may be selected depending upon the dosage, patient condition, cancer type and stage, and other clinical factors.

In another embodiment, a method of treating or retarding or preventing the development of melanoma in a mammalian subject comprises administering to said subject a $BRAF_{V600E}$-based modified peptide or a pharmaceutically acceptable salt thereof and at least one of (a) a T helper peptide and (b) an antibody that binds a checkpoint inhibitor or a synthetic small molecule that mimics the function of a checkpoint inhibitor.

In another embodiment, a method of treating or retarding or preventing the development of melanoma in a mammalian subject comprising administering to said subject a nucleic acid sequence encoding a $BRAF_{V600E}$-based modified peptide and at least one of (a) a nucleic acid sequence encoding a T helper peptide and (b) an antibody that binds a checkpoint inhibitor or a synthetic small molecule that mimics the function of a checkpoint inhibitor.

In still a further embodiment, a method of treating or retarding or preventing the development of melanoma in a mammalian subject comprising administering to said subject a dendritic cell pretreated with a $BRAF_{V600E}$-based modified peptide or nucleic acid sequence encoding said peptide with at least one of (a) a T helper peptide and (b) an antibody that binds a checkpoint inhibitor or a synthetic small molecule that mimics the function of a checkpoint inhibitor. In another embodiment, the dendritic cell is pretreated with the T helper peptide, a fusion of the $BRAF_{V600E}$-based modified peptide with the T helper peptide, or a peptide spanning the T helper and CTL peptides of $BRAF_{V600E}$ as described above. In yet another embodiment, the dendritic cell is pretreated or transfected with nucleic acid molecules encoding these peptides.

A method of treating or preventing the development of a melanoma involves administering to a mammalian subject, preferably a human, an effective amount of a pharmaceutical composition described herein. The amount of the protein, peptide or nucleic acid sequences present in each effective dose is selected with regard to consideration to the half-life of the compound, the identity and/or stage of the melanoma, the patient's age, weight, sex, general physical condition and the like. The amount of active component required to induce an effective CTL response against the melanoma cells without significant adverse side effects varies depending upon the pharmaceutical composition employed and the optional presence of other components. Generally, for the compositions containing protein/peptide, or fusion protein, each dose will comprise between about 5 µg peptide/kg patient body weight to about 10 mg/kg. Generally, a useful therapeutic dosage is between 1 to 5 mg peptide/kg body weight. Another embodiment of a useful dosage may be about 500 µg/kg of peptide. In one embodiment, the composition is administered at a concentration of from and including 25 to 250 micromoles of the peptide or nucleic acid sequence encoding the peptide.

In one embodiment a suitable concentration of the dose of the $BRAF_{V600E}$-based peptide, polypeptide, fusion with T helper or nucleic acid sequences encoding same is administered in at least 1, 5, 10, 20, 30, 40, 50, 60, 70, 80, 90, 100, 110, 120, 130, 140, 150, 160, 170, 180, 190, 200, 210, 220, 230, 240, 250, 260, 270, 280, 290, 300, 310, 320, 330, 340, 350, 360, 370, 380, 390, 400, 410, 420, 430, 440, 450, 460, 470, 480, 490, to at least about 500 µM. Similarly intervening concentration between any two numbers listed is encompassed in the term "suitable concentration. Other dosage ranges may also be contemplated by one of skill in the art. For example, dosages of the peptides may be similar to the dosages discussed for other peptide cancer therapeutics.

If the composition is administered as an antibody or other protein, the dosages may range between a unit dosage of between 0.01 mg to 100 mg of protein (which is equivalent to about 12.5 µg/kg body weight). If any of the compositions are administered as naked DNA, the dosages may range from about 50 µg to about 1 mg of DNA per mL of a sterile solution. If the composition is administered as a DNA vaccine in a virus, a therapeutically effective adult human or veterinary dosage of a viral vector is generally in the range of from about 100 µL to about 100 mL of a carrier containing concentrations of from about $1 \times 10^6$ to about $1 \times 10^{15}$ particles, about $1 \times 10^{11}$ to $1 \times 10^{13}$ particles, or about $1 \times 10^9$ to $1 \times 10^{12}$ particles virus. The dosage of the checkpoint inhibitor may be adjusted based on known toxicities of the particular antibody or small molecule used.

In one embodiment, the selected composition is administered in a single dose. In another embodiment an initial dose of a composition may be optionally followed by repeated administration for a duration selected by the attending physician. In one embodiment, one to three booster doses are administered. Dosage frequency may also depend upon the factors identified above, and may range from 1 to 6 doses per day for a duration of about 3 days to a maximum of no more than about 1 week. The compositions may also be administered as a continuous infusion for about 3-5 days, the specific dosage of the infusion depending upon the half-life of the compound. The compounds may also be incorporated into chemotherapy protocols, involving repetitive cycles of dosing. Selection of the appropriate dosing method would be made by the attending physician.

In another embodiment, the peptide or nucleic acid compositions and checkpoint inhibitors are independently administered systemically by intramuscular, intraperitoneal, intravenous, intratumoral, intranodal or oral administration. In still further embodiments, the subject is treated with other anti-cancer therapies before, during or after treatment with said composition. For example, the subject can be treated with chemotherapy before administering said composition.

In another embodiment, this method involving co-administering the immunotherapeutic compositions with the pre-treated dendritic cell can also include administering a checkpoint inhibitor in the form of an antibody or a small molecule.

In one embodiment described herein, the immunotherapeutic $BRAF_{V600E}$-based peptide, polypeptide or fusion compositions and T helper peptide or nucleic acid compositions encoding them, or dendritic cell pretreated with them are administered substantially simultaneously. In another embodiment, these immunotherapeutic compositions and T helper sequences, optionally with the checkpoint inhibitor, are administered sequentially by the same or different routes of administration. The routes of administration selected depend upon the nature of the compositions. For example, if the checkpoint inhibitor is a small chemical molecule, such molecules may be administered orally in doses known and accepted for other pharmaceutical uses of these drugs. The other compositions or components of the method are administered in different routes as mentioned above.

In still further aspects of these methods, the subject may be treated with other anti-cancer therapies before, during or after treatment with the compositions or individual components of the compositions and methods above-described. Such treatment may be concurrent or simultaneous with the $BRAF_{V600E}$-based peptide or nucleic acid compositions or dendritic cell compositions or overlap treatment with any of these components. In one embodiment, the methods involve treating the subject with chemotherapy before administering the immunotherapeutic compositions, T helper sequences and/or checkpoint inhibitor antibodies or small molecule mimics. In still another embodiment, the method further comprises depleting the subject of lymphocytes and optionally surgically resecting the tumor prior to administration of the components of the above-described methods.

Other dosages are taught in the references recited herein and can be readily adjusted by one of skill in the art depending upon the treatment regimen, physical condition of the patient, type and stage and location of the tumor being treated, and taking into consideration other ancillary chemotherapies being used to treat the patient.

The following examples are provided for the purpose of illustration only and the invention should in no way be construed as being limited to these examples but rather should be construed to encompass any and all variations that become evident as a result of the teaching provided herein.

Example 1: T Helper Sequences

Amino acid sequences upstream and downstream of $BRAF_{V600E}$ mutation were screened for T-helper sequences (Th) that bind to HLA-DR alleles using computer algorithms Table I illustrates a number of sequences tested.

TABLE 1

Human Modified $BRAF_{V600E}$ Peptides Predicted to Bind to HLA-A2

| Peptide | Peptide Sequence (in single letter code) | HLA Binding Score | T2 Binding (FI)[1] | SEQ ID NO: |
|---|---|---|---|---|
| Unmodified 1 | LAT<u>E</u>KSRWS | 8 | 0.93 | 22 |
| Unmodified 2 | LAT<u>E</u>KSRWSG | 9 | 1.1 | 2 |
| Modified 1 | LIT<u>E</u>KSRWSG | 13 | 1.0 | 23 |
| Modified 2 | LMT<u>E</u>KSRWSG | 13 | 0.8 | 24 |
| Modified 3 | LLT<u>E</u>KSRWSG | 15 | 0.9 | 25 |
| Modified 4 | LLT<u>E</u>KSRWSV | 25 | 6.5 | 26 |
| Modified 5 | LAT<u>E</u>KSRWSI | 17 | 0.7 | 27 |
| Modified 6 | LAT<u>E</u>KSRWSL | 19 | 0.6 | 28 |
| Modified 7 | LAT<u>E</u>KSRWSV | 19 | 1.0 | 29 |
| Neg control | SEERFEIFPKE | 5 | 0.93 | 30 |
| Pos control | NLVPMVATV | 30 | 9.9 | 31 |

[1] FI = ($MFI_{peptide}/MFI_{w/o\ peptide}$) -1

A number of such peptides were assayed as follows: Adherent monocytes ($5 \times 10^4$/well) were pulsed for 8 hours with synthetic peptides (25 µM): Peptide 8 (SEQ ID NO:15), Peptide 9 (SEQ ID NO:16), and Peptide 10 (SEQ ID NO: 17). At the end of incubation, excess peptides were removed and the monocytes were cultured with one of three melanoma patient PBMC samples labeled WM35, WM3457 and 3451 ($1\times10^5$) for 5 days.

Proliferative responses were determined by standard $^3$HTdR incorporation assay and the results shown in FIG. 1. Data are expressed as mean cpm (triplicate determinations) plus SD (bar) of $^3$HTdR incorporation. Significantly ($p<0.01$) different values compared to control were obtained in this assay with either Peptide 8 or Peptide 9 in each sample assayed. Thus, T helper peptides were shown to induce proliferative response in melanoma patients PBMCs.

Example 2: Induction of Cytotoxic T Cells

Adherent monocytes ($5\times10^4$/well) were pulsed for 8 h with T-helper synthetic peptides (25 μM) either alone or in combination with an affinity modified $BRAF_{V600E}$-based peptide, i.e., a CTL peptide of the sequence LMTEKSRWSG (SEQ ID NO: 25). Cell cultures were initiated as described in Example 1 and at the end of 7 days T-cells were harvested and stained with fluorescence conjugated anti-CD4 or anti-CD8 antibodies and analyzed for T-cell binding by standard FACS assay.

Figure 2:
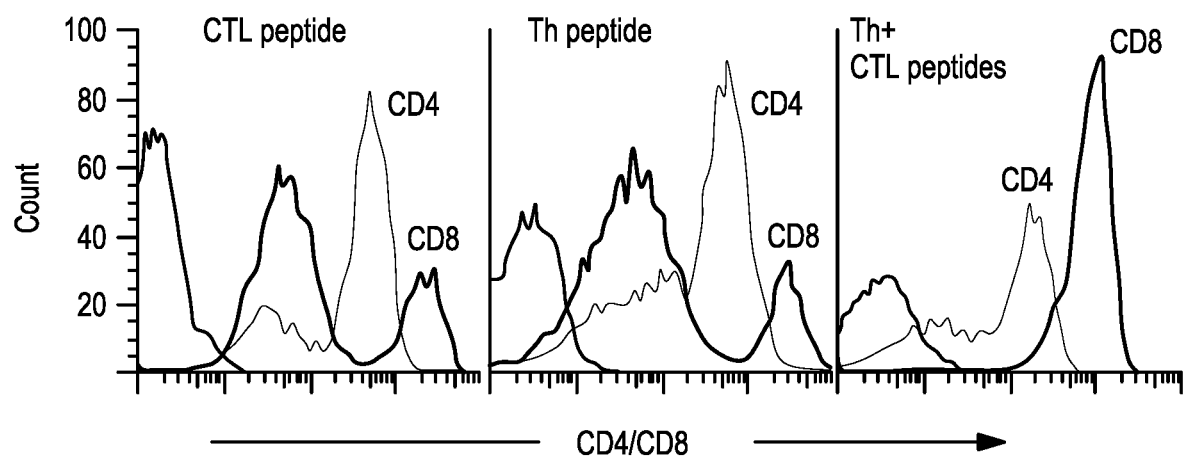
FIG. 2 is a graph showing the induction of enriched CD8 cytotoxic T cells (CTLs) in the presence of both a T helper and a BRAF$_{V600E}$-based CTL peptide. The BRAF$_{V600E}$-based CTL peptide is that of the sequence LMTEKSRWSG (SEQ ID NO: 25). The T helper sequence is that of P9 (SEQ ID NO: 16). According to the process of Example 2, adherent monocytes were pulsed with the T helper synthetic peptides (25 µM) either alone or in combination with the affinity modified BRAF$_{V600E}$-based CTL peptide and cell cultured. T-cells were harvested and stained with anti-CD4 or anti-CD8 antibodies and analyzed for T-cell binding by standard FACS assay.

As shown in FIG. 2, the Th peptides induced enriched CD8 CTLs in the presence of both the Th peptide and the $BRAF_{V600E}$-based CTL peptide.

Example 3: Induction of More Potent CTLs

T-cell cultures were initiated as described in Examples 1 and 2. After 7 days, growing lymphocyte cultures were harvested and restimulated with Th peptide 9 of sequence EDLTVKIGDFGLATV (SEQ ID NO:16), the $BRAF_{V600E}$-based peptide of SEQ ID NO: 25, or both, and 20 U/ml of natural human IL-2. This process was repeated every 7 days until day 56 when lymphocytes were harvested and tested for cytolytic activity against HLA-A2+ autologous WM35 (V600E+) or HLA-A2+ matched allogeneic WM3456 (V600E−) melanoma cells in standard $^{51}$Cr-release assay. Varied effector (T-cells) to tumor target ratios of 12.5:1 or 25:1 or 50:1 were used in the assay.

Figure 3:
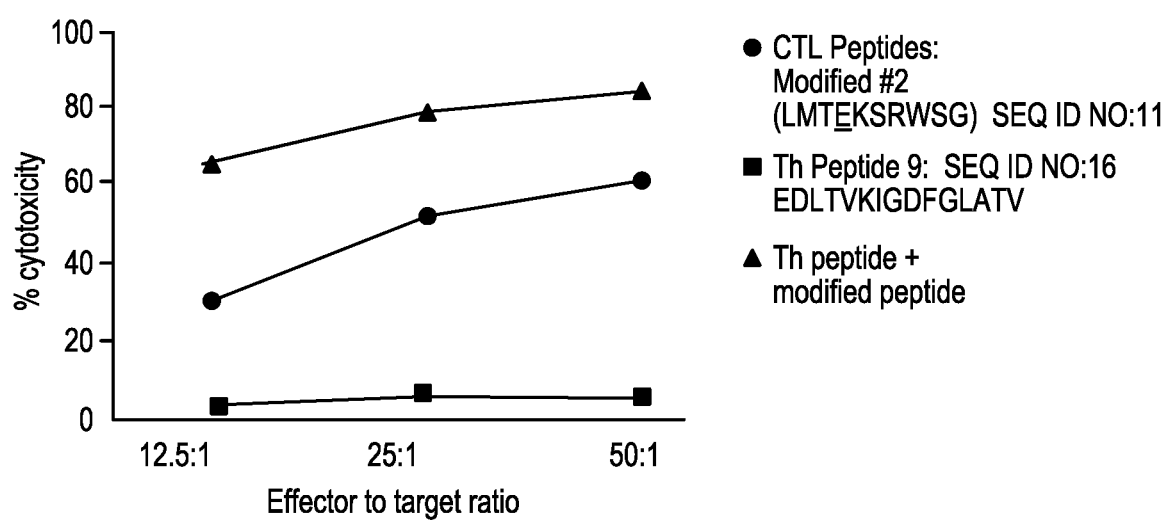
FIG. 3 is a graph showing the results of a standard $^{51}$Cr-release assay conducted on melanoma cells exposed to lymphocytes that had been stimulated with Th peptide P9 (SEQ ID NO: 16) identified above in FIG. 1, the BRAF$_{V600E}$-based CTL peptide (SEQ ID NO: 25), or both peptides and with natural human IL-2, as described in Example 3. The lymphocytes were tested for cytolytic activity against HLA-A2+ autologous WM35 (V600E+) or HLA-A2+ matched allogeneic WM3456 (V600E−) melanoma cells. Indicated effector (T-cells) to tumor target ratios were used in the assay.

As shown in FIG. 3, a combination of the T helper and $BRAF_{V600E}$-based CTL peptide induces more potent CTLs than either the Th or CTL peptides alone.

Example 4: Regression of Established Tumor

In an established tumor model, C57Bl/6 (4-6 weeks old; n=5; male) mice received s.c. injection of mouse melanoma cell line (YUMM 1.7; $1\times10^5$). After 7 days the tumor was established. Mice received $BRAF_{V600E}$-based peptide (SEQ ID NO:25) immunization (50 μg, intradermally, every 7 days) in presence of CpG (30 μg) as adjuvant. Mice also received anti-PD-1 antibody (250 μg via intraperitoneal injection, every 5-6 days) either alone or in combination.

Figure 4:
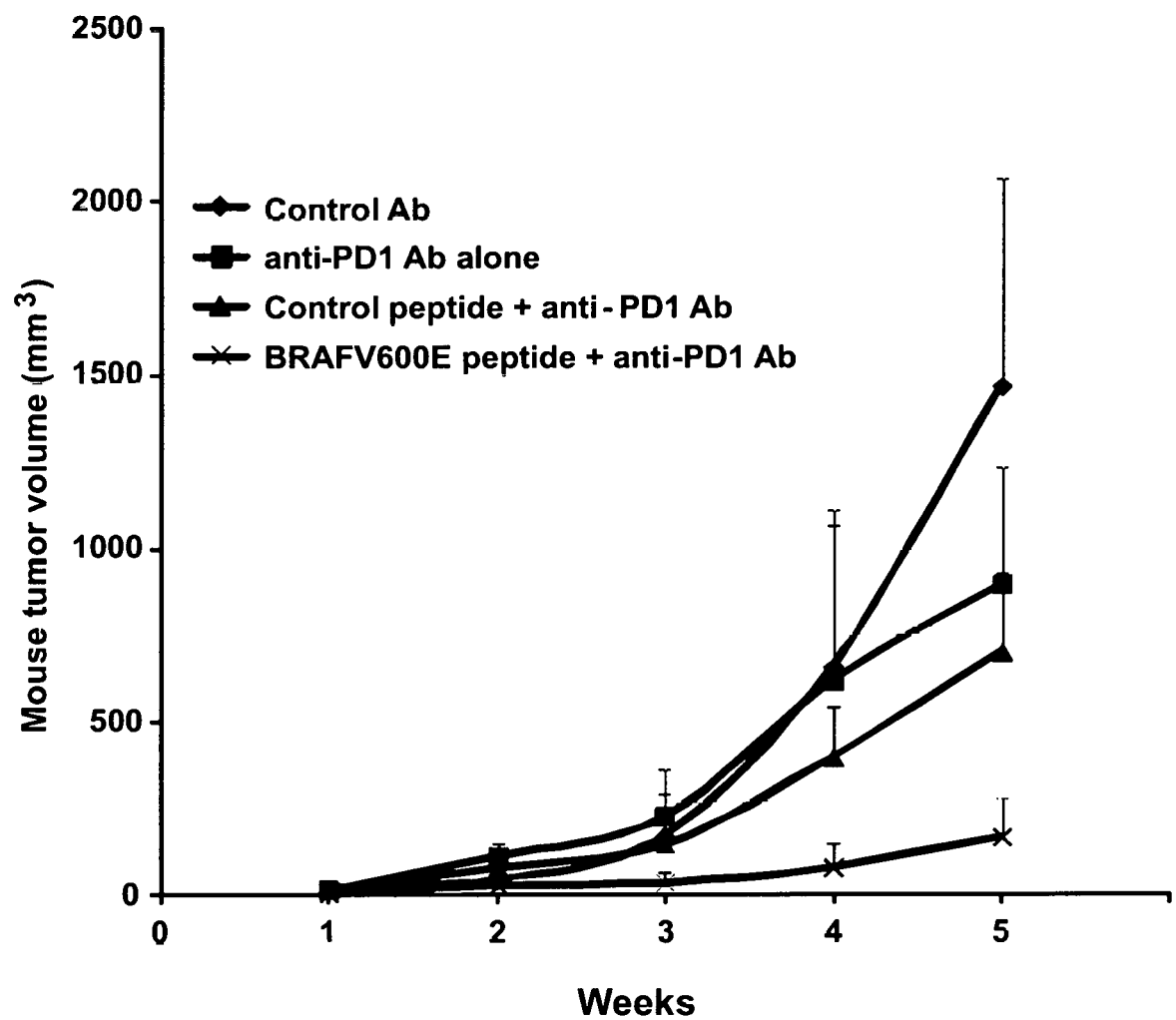
FIG. 4 is a graph showing the effect of a BRAF$_{V600E}$-based CTL peptide (SEQ ID NO: 25), and a checkpoint inhibitor, which is an anti-programmed cell death protein 1 (PD-1) antibody, in an established tumor model described in Example 4. Tumor growth measurements are shown as Mean tumor volume and SEM and the results are compared with mice that received control HIV peptide and anti-PD-1 antibody. Combination of peptide immunization and anti-PD-1 antibody therapy showed significant inhibition of tumor growth (p<0.05). Anti-PD-1 antibody alone was not effective in tumor inhibition when compared to isotype control antibody treatment.

FIG. 4 shows tumor growth measurements as mean tumor volume and SEM. The results are compared with mice that received control HIV peptide and anti-PD-1 antibody. Combination of peptide immunization and anti-PD-1 antibody therapy showed significant inhibition of tumor growth ($p<0.05$). Anti-PD-1 antibody alone was not effective in tumor inhibition when compared to isotype control antibody treatment. FIG. 4 demonstrates that a combination of immunization with a $BRAF_{V600E}$-based CTL peptide and treatment with a checkpoint inhibitor, i.e., anti-PD-1 antibody, has significant effect on growth of mouse melanoma (YUMM 1.7) cells in an established tumor model and induces regression of established tumor.

TABLE 2

(Sequence Listing Free Text)

| SEQ ID NO: (containing free text) | | Free text under <223> |
|---|---|---|
| 2 | <210> | 2 |
| | <211> | 10 |
| | <212> | PRT |
| | <213> | Artificial Sequence |
| | <220> | |
| | <223> | synthetic peptide |
| 3 | <210> | 3 |
| | <211> | 14 |
| | <212> | PRT |
| | <213> | Artificial Sequence |
| | <220> | |
| | <223> | synthetic peptide |
| | <220> | |
| | <221> | MISC_FEATURE |
| | <222> | (1)..(2) |
| | <223> | Xaa is absent, Ser, Gly or Cys |
| | <220> | |
| | <221> | MISC_FEATURE |
| | <222> | (4)..(4) |
| | <223> | Xaa is a substituted or unsubstituted Ala, Leu, Met, Val, Pro or Gly |
| | <220> | |
| | <221> | MISC_FEATURE |
| | <222> | (5)..(5) |
| | <223> | Xaa is a substituted or unsubstituted Thr or Ser |
| | <220> | |

TABLE 2-continued (Sequence Listing Free Text)

| SEQ ID NO: (containing free text) | Free text under <223> |
|---|---|

|   | <221> | MISC_FEATURE |
|---|---|---|
|   | <222> | (7)..(7) |
|   | <223> | Xaa is a substituted or unsubstituted Lys, Arg or His |
|   | <220> | |
|   | <221> | MISC_FEATURE |
|   | <222> | (8)..(8) |
|   | <223> | Xaa is a substituted or unsubstituted Ser or Thr |
|   | <220> | |
|   | <221> | MISC_FEATURE |
|   | <222> | (9)..(9) |
|   | <223> | Xaa is a substituted or unsubstituted Arg, Lys, or His |
|   | <220> | |
|   | <221> | MISC_FEATURE |
|   | <222> | (11)..(11) |
|   | <223> | Xaa is substituted or unsubstituted Thr, Val, Leu or Ser |
|   | <220> | |
|   | <221> | MISC_FEATURE |
|   | <222> | (12)..(12) |
|   | <223> | Xaa is absent or is a substituted or unsubstituted Gly, Pro or Leu |
|   | <220> | |
|   | <221> | MISC_FEATURE |
|   | <222> | (13)..(14) |
|   | <223> | Xaa is absent or is a Cys, Ser or Gly |
| 4 | <210> | 4 |
|   | <211> | 14 |
|   | <212> | PRT |
|   | <213> | Artificial Sequence |
|   | <220> | |
|   | <223> | synthetic peptide |
|   | <220> | |
|   | <221> | MISC_FEATURE |
|   | <222> | (1)..(2) |
|   | <223> | Xaa is Ser, Gly, Cys or absent |
|   | <220> | |
|   | <221> | MISC_FEATURE |
|   | <222> | (4)..(4) |
|   | <223> | Xaa is a substituted or unsubstituted Ile |
|   | <220> | |
|   | <221> | MISC_FEATURE |
|   | <222> | (12)..(12) |
|   | <223> | Xaa is a substituted or unsubstituted Gly, Ala, Val, Leu, Ile, Pro, Phe, Met or Trp |
|   | <220> | |
|   | <221> | MISC_FEATURE |
|   | <222> | (13)..(14) |
|   | <223> | Xaa is Ser, Gly, Cys or absent |
| 5 | <211> | 14 |
|   | <212> | PRT |
|   | <213> | Artificial Sequence |
|   | <220> | |
|   | <223> | Synthetic peptide |
|   | <220> | |
|   | <221> | MISC_FEATURE |
|   | <222> | (1)..(2) |
|   | <223> | Xaa is absent, Gly, Ser or Cys |
|   | <220> | |
|   | <221> | MISC_FEATURE |
|   | <222> | (4)..(4) |
|   | <223> | Xaa is a substituted or unsubstituted Gly, Ala, Val, Leu, Ile, Pro, Phe, Met or Trp |
|   | <220> | |
|   | <221> | MISC_FEATURE |
|   | <222> | (12)..(12) |
|   | <223> | Xaa is a substituted or unsubstituted Gly, Val or Leu |
|   | <220> | |
|   | <221> | MISC_FEATURE |
|   | <222> | (13)..(14) |
|   | <223> | Xaa is absent or a Cys, Gly or Ser |

TABLE 2-continued (Sequence Listing Free Text)

| SEQ ID NO: (containing free text) | Free text under <223> |
|---|---|
| 6 | <211> 14<br><212> PRT<br><213> Artificial Sequence<br><220><br><223> synthetic peptide<br><220><br><221> MISC_FEATURE<br><222> (1)..(2)<br><223> Xaa is absent or Gly, Ser or Cys<br><220><br><221> MISC_FEATURE<br><222> (4)..(4)<br><223> Xaa is a substituted or unsubstituted Ala, Ile, Met, or Leu,<br><220><br><221> MISC_FEATURE<br><222> (12)..(12)<br><223> Xaa is a substituted or unsubstituted Gly, Ile, Val or Leu.<br><220><br><221> MISC_FEATURE<br><222> (13)..(14)<br><223> Xaa is absent, Gly, Ser or Cys |
| 7 | <211> 14<br><212> PRT<br><213> Artificial Sequence<br><220><br><223> synthetic peptide<br><220><br><221> MISC_FEATURE<br><222> (1)..(2)<br><223> Xaa is absent, Gly, Ser or Cys<br><220><br><221> MISC_FEATURE<br><222> (13)..(14)<br><223> Xaa is absent, Gly, Ser or Cys |
| 8 | <211> 14<br><212> PRT<br><213> Artificial Sequence<br><220><br><223> synthetic peptide<br><220><br><221> MISC_FEATURE<br><222> (1)..(2)<br><223> Xaa is absent, Gly, Ser or Cys<br><220><br><221> MISC_FEATURE<br><222> (13)..(14)<br><223> Xaa is absent, Gly, Ser or Cys |
| 9 | <211> 14<br><212> PRT<br><213> Artificial Sequence<br><220><br><223> synthetic peptide<br><220><br><221> MISC_FEATURE<br><222> (1)..(2)<br><223> Xaa is absent, Gly, Ser or Cys<br><220><br><221> MISC_FEATURE<br><222> (13)..(14)<br><223> Xaa is absent, Gly, Ser or Cys |
| 10 | <211> 14<br><212> PRT<br><213> Artificial Sequence<br><220><br><223> synthetic peptide<br><220> |

TABLE 2-continued (Sequence Listing Free Text)

| SEQ ID NO: (containing free text) | Free text under <223> | |
|---|---|---|
| | <221> | MISC_FEATURE |
| | <222> | (1)..(2) |
| | <223> | Xaa is absent, Gly, Ser or Cys |
| | <220> | |
| | <221> | MISC_FEATURE |
| | <222> | (13)..(14) |
| | <223> | Xaa is absent, Gly, Ser or Cys |
| 11 | <211> | 14 |
| | <212> | PRT |
| | <213> | Artificial Sequence |
| | <220> | |
| | <223> | synthetic peptide |
| | <220> | |
| | <221> | MISC_FEATURE |
| | <222> | (1)..(2) |
| | <223> | Xaa is absent, Gly, Ser or Cys |
| | <220> | |
| | <221> | MISC_FEATURE |
| | <222> | (13)..(14) |
| | <223> | Xaa is absent, Gly, Ser or Cys |
| 12 | <211> | 14 |
| | <212> | PRT |
| | <213> | Artificial Sequence |
| | <220> | |
| | <223> | synthetic peptide |
| | <220> | |
| | <221> | MISC_FEATURE |
| | <222> | (1)..(2) |
| | <223> | Xaa is absent, Gly, Ser or Cys |
| | <220> | |
| | <221> | MISC_FEATURE |
| | <222> | (13)..(14) |
| | <223> | Xaa is absent, Gly, Ser or Cys |
| 13 | <211> | 14 |
| | <212> | PRT |
| | <213> | Artificial Sequence |
| | <220> | |
| | <223> | synthetic peptide |
| | <220> | |
| | <221> | MISC_FEATURE |
| | <222> | (1)..(2) |
| | <223> | Xaa is absent, Gly, Ser or Cys |
| | <220> | |
| | <221> | MISC_FEATURE |
| | <222> | (13)..(14) |
| | <223> | Xaa is absent, Gly, Ser or Cys |
| 14 | <211> | 14 |
| | <212> | PRT |
| | <213> | Artificial Sequence |
| | <220> | |
| | <223> | synthetic peptide |
| | <220> | |
| | <221> | MISC_FEATURE |
| | <222> | (1)..(2) |
| | <223> | Xaa is absent, Gly, Ser or Cys |
| | <220> | |
| | <221> | MISC_FEATURE |
| | <222> | (13)..(14) |
| | <223> | Xaa is absent, Gly, Ser or Cys |
| 18 | <211> | 21 |
| | <212> | PRT |
| | <213> | Artificial Sequence |
| | <220> | |
| | <223> | synthetic peptide |
| | <220> | |
| | <221> | MISC_FEATURE |
| | <222> | (13)..(13) |
| | <223> | Xaa is a substituted or unsubstituted Ala, Ile, Met, Leu, Gly, Val, Pro, Phe, or Trp |

TABLE 2-continued (Sequence Listing Free Text)

| SEQ ID NO: (containing free text) | | Free text under <223> |
|---|---|---|
| | <220> <221> <222> <223> | MISC_FEATURE (21)..(21) Xaa is a substituted or unsubstituted Ala, Ile, Met, Leu, Gly, Val, Pro, Phe, or Trp |
| 19 | <211> <212> <213> <220> <223> <220> <221> <222> <223> <220> <221> <222> <223> | 20 PRT Artificial Sequence  synthetic peptide  MISC_FEATURE (12)..(12) Xaa is a substituted or unsubstituted Ala, Ile, Met, Leu, Gly, Val, Pro, Phe, or Trp  MISC_FEATURE (20)..(20) Xaa is a substituted or unsubstituted Ala, Ile, Met, Leu, Gly, Val, Pro, Phe, or Trp |
| 20 | 211> <212> <213> <220> <223> <220> <221> <222> <223> <220> <221> <222> <223> | 26 PRT Artificial Sequence  synthetic peptide  MISC_FEATURE (2)..(2) Xaa is a substituted or unsubstituted Ala, Ile, Met, Leu, Gly, Val, Pro, Phe, or Trp  MISC_FEATURE (10)..(10) Xaa is a substituted or unsubstituted Ala, Ile, Met, Leu, Gly, Val, Pro, Phe, or Trp |
| 22 | <211> <212> <213> <220> <223> | 9 PRT Artificial Sequence  synthetic peptide |
| 23 | <211> <212> <213> <220> <223> | 10 PRT Artificial Sequence  synthetic peptide |
| 24 | <211> <212> <213> <220> <223> | 10 PRT Artificial Sequence  synthetic peptide |
| 25 | <211> <212> <213> <220> <223> | 10 PRT Artificial Sequence  synthetic peptide |
| 26 | <211> <212> <213> <220> <223> | 10 PRT Artificial Sequence  synthetic peptide |
| 27 | <211> <212> <213> <220> <223> | 10 PRT Artificial Sequence  synthetic peptide |

TABLE 2-continued (Sequence Listing Free Text)

| SEQ ID NO: (containing free text) | | Free text under <223> |
|---|---|---|
| 28 | <211> <212> <213> <220> <223> | 10 PRT Artificial Sequence  synthetic peptide |
| 29 | <211> <212> <213> <220> <223> | 10 PRT Artificial Sequence  synthetic peptide |
| 30 | <211> <212> <213> <220> <223> | 11 PRT Artificial Sequence  synthetic peptide |
| 31 | 211> <212> <213> <220> <223> | 9 PRT Artificial Sequence  synthetic peptide |
| 32 | <211> <212> <213> <220> <223> | 26 PRT Artificial Sequence  synthetic peptide |
| 33 | <211> <212> <213> <220> <223> | 20 PRT Artificial Sequence  synthetic peptide |
| 34 | <211> <212> <213> <220> <223> | 19 PRT Artificial Sequence  synthetic peptide |

The following information is provided for sequences containing free text under numeric identifier <223>.

Each and every patent, patent application, including U.S. Provisional Patent Application No. 62/296,705, and publication, including NCBI sequences, the sequence listing and websites cited throughout the disclosure and listed below, is expressly incorporated herein by reference in its entirety. All publicly available documents and public databases and publicly available DNA and nucleic acid sequences cited within this specification are incorporated herein by reference. The claims and the sequence listing are incorporated herein by reference. While this invention has been disclosed with reference to specific embodiments, it is apparent that other embodiments and variations of this invention are devised by others skilled in the art without departing from the true spirit and scope of the invention. The appended claims include such embodiments and equivalent variations.

The invention claimed is:

1. A composition comprising (a) a first peptide or a pharmaceutically acceptable salt thereof, the first peptide having the formula
   (a1)   Xaa1-Xaa2-Leu-Xaa4-Thr-Glu-Lys-Ser-Arg-Trp-Ser-Xaa12-Xaa13-Xaa14 (SEQ ID NO: 4), wherein Xaa1, Xaa2, Xaa13 and Xaa14, are each independently absent, Ser, Gly, or Cys for coupling to an additional peptide or protein, and wherein Xaa4 is a substituted or unsubstituted Ile and Xaa12 is a hydrophobic amino acid;
   (a2)   Xaa1-Xaa2-Leu-Xaa4-Thr-Glu-Lys-Ser-Arg-Trp-Ser-Xaa12-Xaa13-Xaa14 (SEQ ID NO: 5), wherein Xaa1, Xaa2, Xaa13 and Xaa14, are each independently absent, Ser, Gly, or Cys for coupling to an additional peptide or protein, and wherein Xaa4 is a hydrophobic amino acid and Xaa12 is a substituted or unsubstituted Gly, Val, or Leu; or
   (a3)   Xaa1-Xaa2-Leu-Xaa4-Thr-Glu-Lys-Ser-Arg-Trp-Ser-Xaa12-Xaa13-Xaa14 (SEQ ID NO: 6), wherein Xaa1, Xaa2, Xaa13 and Xaa14, are each independently absent, Ser, Gly, or Cys for coupling to an additional peptide or protein, and wherein Xaa4 is a substituted or unsubstituted Ile, Ala, Met, or Leu, and wherein Xaa12 is a substituted or unsubstituted Gly, Ile, Val, or Leu; and
   (b) an antibody or fragment of said antibody that binds a programmed cell death protein 1 (PD-1) checkpoint inhibitor.

2. The composition according to claim 1, wherein the hydrophobic amino acid is a substituted or unsubstituted Gly, Ala, Val, Leu, Ile, Pro, Phe, Met, or Trp.

3. The composition according to claim 1, further comprising a pharmaceutically acceptable vehicle or carrier.

4. The composition according to claim 1, wherein in the first peptide of formula (a1) Xaa12 is a substituted or unsubstituted Gly, Val, or Leu; or in the first peptide (a2) Xaa4 is a substituted or unsubstituted Ile, Ala, Met, or Leu.

5. The composition according to claim 1, wherein said first peptide is

```
                                            (SEQ ID NO: 7)
Xaa1-Xaa2-Leu-Ile-Thr-Glu-Lys-Ser-Arg-Trp-Ser-
Gly-Xaa13-Xaa14;

(SEQ ID NO: 8)
Xaa1-Xaa2-Leu-Ile-Thr-Glu-Lys-Ser-Arg-Trp-Ser-
Val-Xaa13-Xaa14;

(SEQ ID NO: 9)
Xaa1-Xaa2-Leu-Leu-Thr-Glu-Lys-Ser-Arg-Trp-Ser-
Val-Xaa13-Xaa14;

(SEQ ID NO: 10)
Xaa1-Xaa2-Leu-Ala-Thr-Glu-Lys-Ser-Arg-Trp-Ser-
Ile-Xaa13-Xaa14;

(SEQ ID NO: 11)
Xaa1-Xaa2-Leu-Met-Thr-Glu-Lys-Ser-Arg-Trp-Ser-
Gly-Xaa13-Xaa14 or (SEQ ID NO: 12)
Xaa1-Xaa2-Leu-Ala-Thr-Glu-Lys-Ser-Arg-Trp-Ser-
Val-Xaa13-Xaa14,
```
wherein Xaa1, Xaa2, Xaa13, and Xaa14 are each independently absent, Ser, Gly, or Cys for coupling to an additional peptide or protein.

6. The composition according to claim 1, wherein each said Xaa1 and Xaa13 is Cys and each said Xaa2 and Xaa14 is absent.

7. The composition according to claim 1, comprising a T helper peptide or a pharmaceutically acceptable salt thereof, wherein said T helper peptide is

```
                                           (SEQ ID NO: 15)
Ser-His-Gln-Phe-Glu-Gln-Leu-Ser-Gly-Ser-Ile-Leu-
Trp-His-Ala;

(SEQ ID NO: 16)
Glu-Asp-Leu-Thr-Val-Lys-Ile-Gly-Asp-Phe-Gly-Leu-
Ala-Thr-Val; or (SEQ ID NO: 17)
Asp-Leu-Thr-Val-Lys-Ile-Gly-Asp-Phe-Gly-Leu-Ala-
Thr-Val-Lys.
```

8. The composition according to claim 7, wherein said T cell peptide is coupled or fused at either the N- or C-termini of the first peptide.

9. The composition according to claim 1, further comprising a liposome or an adjuvant.

10. The composition according to claim 1, wherein the first peptide has the formula Xaa1-Xaa2-Leu-Xaa4-Thr-Glu-Lys-Ser-Arg-Trp-Ser-Xaa12-Xaa13-Xaa14 (SEQ ID NO: 6), wherein Xaa1 is Gly, Xaa2 is absent, Xaa13 is Ser, Xaa14 is absent, Xaa4 is unsubstituted Met, and Xaa12 is unsubstituted Gly.

11. The composition according to claim 10, further comprising a T helper peptide (SEQ ID NO: 16).

12. The composition according to claim 1, wherein the antibody to PD-1 is nivolumab (CAS 946414-94-4).

13. A method of treating or retarding melanoma in a mammalian subject comprising administering to a subject in need thereof a composition of claim 1.

14. The method according to claim 13, wherein the first peptide (a) and the antibody (b) are independently administered.

* * * * *

UNITED STATES PATENT AND TRADEMARK OFFICE
CERTIFICATE OF CORRECTION

| | | |
|---|---|---|
| PATENT NO. | : 11,208,468 B2 | Page 1 of 1 |
| APPLICATION NO. | : 15/998913 | |
| DATED | : December 28, 2021 | |
| INVENTOR(S) | : Somasundaram et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 191 days.

Signed and Sealed this
Twenty-fifth Day of February, 2025

Coke Morgan Stewart
*Acting Director of the United States Patent and Trademark Office*